(12) United States Patent
O'Connor et al.

(10) Patent No.: US 11,963,702 B2
(45) Date of Patent: *Apr. 23, 2024

(54) APPARATUS AND METHOD FOR JOINT REPAIR

(71) Applicant: Smith & Nephew, Inc., Memphis, TN (US)

(72) Inventors: Paul O'Connor, Norfolk, MA (US); Michael Charles Ferragamo, Foster, RI (US); William R. Davis, Hingham, MA (US); Rajesh Sivakumar, Ashland, MA (US)

(73) Assignee: Smith & Nephew, Inc., Memphis, TN (US)

( * ) Notice: Subject to any disclaimer, the term of this patent is extended or adjusted under 35 U.S.C. 154(b) by 353 days.

This patent is subject to a terminal disclaimer.

(21) Appl. No.: 17/361,665

(22) Filed: Jun. 29, 2021

(65) Prior Publication Data

US 2022/0022927 A1    Jan. 27, 2022

Related U.S. Application Data

(63) Continuation of application No. 16/255,248, filed on Jan. 23, 2019, now Pat. No. 11,045,233, which is a
(Continued)

(51) Int. Cl.
*A61B 17/80* (2006.01)
*A61B 17/04* (2006.01)
(Continued)

(52) U.S. Cl.
CPC ...... *A61B 17/8038* (2013.01); *A61B 17/0401* (2013.01); *A61B 17/1615* (2013.01);
(Continued)

(58) Field of Classification Search
CPC . A61B 17/80; A61B 17/8038; A61B 17/8057; A61B 17/68; A61B 17/84;
(Continued)

(56) References Cited

U.S. PATENT DOCUMENTS

| | | |
|---|---|---|
| 5,921,986 A | 7/1999 | Bonutti |
| 6,306,159 B1 | 10/2001 | Schwartz et al. |

(Continued)

FOREIGN PATENT DOCUMENTS

| | | |
|---|---|---|
| EP | 1016377 A2 | 7/2000 |
| EP | 2792324 A1 | 10/2014 |

(Continued)

OTHER PUBLICATIONS

International Search Report; European Patent Office; International Application No. PCT/US2016/055116; dated Feb. 8, 2017; 8 pages.

(Continued)

*Primary Examiner* — Christopher J Beccia
(74) *Attorney, Agent, or Firm* — Taft Stettinius & Hollister LLP

(57) ABSTRACT

A bolster system having a first bolster device, a second bolster device, and an adjustable tether that includes a one-way pre-tied slideable adjustment knot. The adjustment knot is at a first position prior to insertion of the first bolster device into a passageway in one or more bones. The second bolster device includes a body portion having an outer portion that is sized to be received in the passageway and/or in an aperture of a bone plate. The body portion also includes a channel that is sized to accommodate recessed and/or embedded placement of the pre-tied slideable adjustment knot. The second bolster device can also include an oversized plate portion that abuts against a cortex of a bone or a wall of a bone plate. The second bolster device can also
(Continued)

include a threaded member or retention tab that lockingly secures the second bolster device to a bone plate.

18 Claims, 16 Drawing Sheets

Related U.S. Application Data continuation of application No. 15/764,638, filed as application No. PCT/US2016/055116 on Oct. 3, 2016, now Pat. No. 10,779,868.

(60) Provisional application No. 62/238,845, filed on Oct. 8, 2015.

(51) Int. Cl.
*A61B 17/16* (2006.01)
*A61B 17/68* (2006.01)
*A61B 17/84* (2006.01)
*A61B 17/06* (2006.01)
*A61B 17/17* (2006.01)

(52) U.S. Cl.
CPC ............ *A61B 17/683* (2013.01); *A61B 17/80* (2013.01); *A61B 17/8057* (2013.01); *A61B 17/842* (2013.01); *A61B 2017/0403* (2013.01); *A61B 2017/0404* (2013.01); *A61B 2017/0406* (2013.01); *A61B 2017/0414* (2013.01); *A61B 2017/0417* (2013.01); *A61B 2017/0427* (2013.01); *A61B 2017/044* (2013.01); *A61B 2017/0475* (2013.01); *A61B 2017/06019* (2013.01); *A61B 17/17* (2013.01)

(58) Field of Classification Search
CPC ..... A61B 17/683; A61B 17/842; A61B 17/16; A61B 17/1615; A61B 17/04; A61B 17/0401
See application file for complete search history.

(56) References Cited

U.S. PATENT DOCUMENTS

| | | | |
|---|---|---|---|
| 6,319,271 B1 * | 11/2001 | Schwartz | ........... A61B 17/0487 606/232 |
| 7,235,091 B2 | 6/2007 | Thomes | |
| 7,875,058 B2 | 1/2011 | Holmes, Jr. | |
| 7,901,431 B2 | 3/2011 | Shumas | |
| 7,963,966 B2 | 6/2011 | Cole | |
| 8,348,960 B2 | 1/2013 | Michel et al. | |
| 8,398,678 B2 | 3/2013 | Baker et al. | |
| 8,425,554 B2 | 4/2013 | Denove et al. | |
| 8,512,376 B2 | 8/2013 | Thomes | |
| 8,814,904 B2 | 8/2014 | Bennett | |
| 9,179,950 B2 | 11/2015 | Zajac et al. | |
| 10,779,868 B2 * | 9/2020 | O'Connor | ............ A61B 17/842 |
| 2002/0161439 A1 | 10/2002 | Strobel et al. | |
| 2007/0073293 A1 | 3/2007 | Martz et al. | |
| 2008/0046009 A1 | 2/2008 | Albertorio et al. | |
| 2009/0198287 A1 | 8/2009 | Chiu | |
| 2010/0211075 A1 | 8/2010 | Stone | |
| 2010/0262185 A1 * | 10/2010 | Gelfand | ................ A61F 2/0811 606/232 |
| 2011/0112576 A1 * | 5/2011 | Nguyen | ............. A61B 17/0401 606/232 |
| 2011/0306989 A1 | 12/2011 | Darois et al. | |
| 2012/0123474 A1 | 5/2012 | Zajac et al. | |
| 2013/0030480 A1 | 1/2013 | Donate et al. | |
| 2013/0053897 A1 | 2/2013 | Brown et al. | |
| 2013/0123810 A1 | 5/2013 | Brown et al. | |
| 2013/0123841 A1 | 5/2013 | Lyon | |
| 2013/0172944 A1 | 7/2013 | Fritzinger et al. | |
| 2013/0331886 A1 | 12/2013 | Thomes | |
| 2014/0074239 A1 | 3/2014 | Albertorio et al. | |
| 2014/0257294 A1 | 9/2014 | Gedet et al. | |
| 2015/0039029 A1 | 2/2015 | Wade | |
| 2015/0051601 A1 | 2/2015 | Larsen et al. | |
| 2016/0030035 A1 | 2/2016 | Zajac et al. | |
| 2016/0051250 A1 | 2/2016 | Thomes | |

FOREIGN PATENT DOCUMENTS

| | | |
|---|---|---|
| WO | 2005110244 A1 | 11/2005 |
| WO | 2011040917 A1 | 4/2011 |
| WO | 2012092027 A2 | 7/2012 |

OTHER PUBLICATIONS

Written Opinion of the International Searching Authority; European Patent Office; International Application No. PCT/US2016/055116; dated Feb. 8, 2017; 11 pages.

European Examination & Search Report, Application No. 167823356.2-1122 dated May 22, 2019.

* cited by examiner

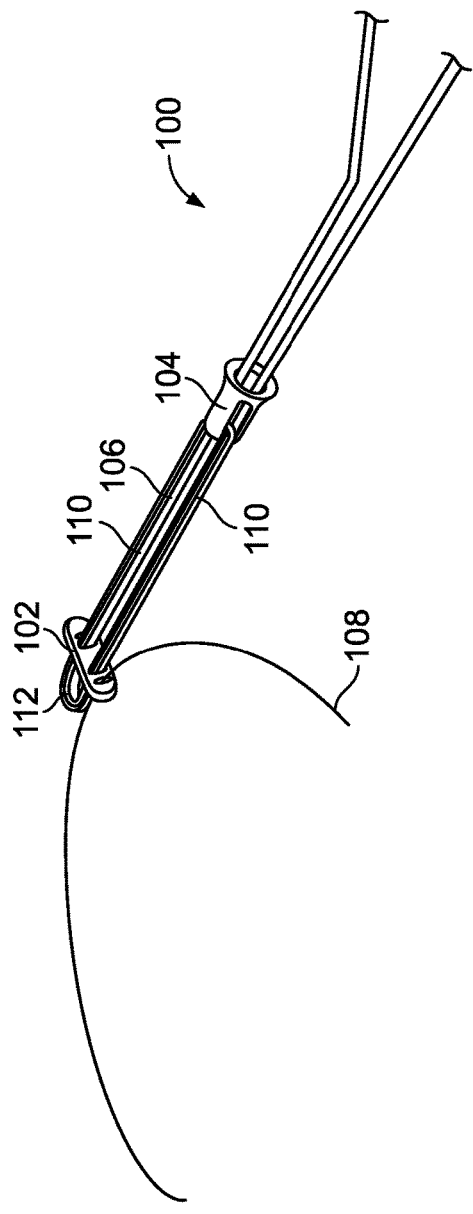
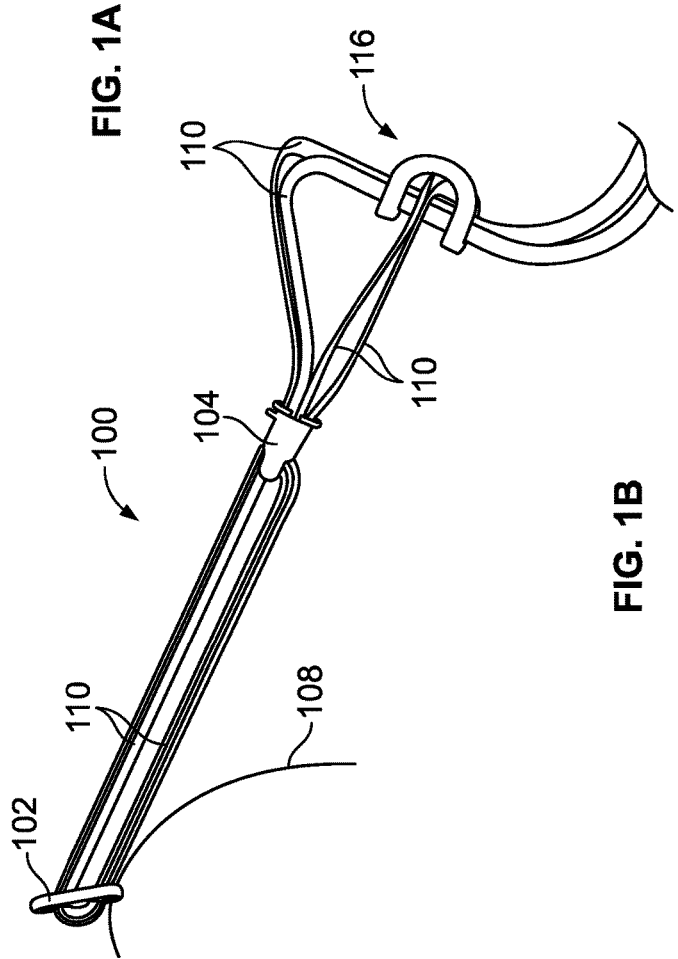
FIG. 1A
FIG. 1B

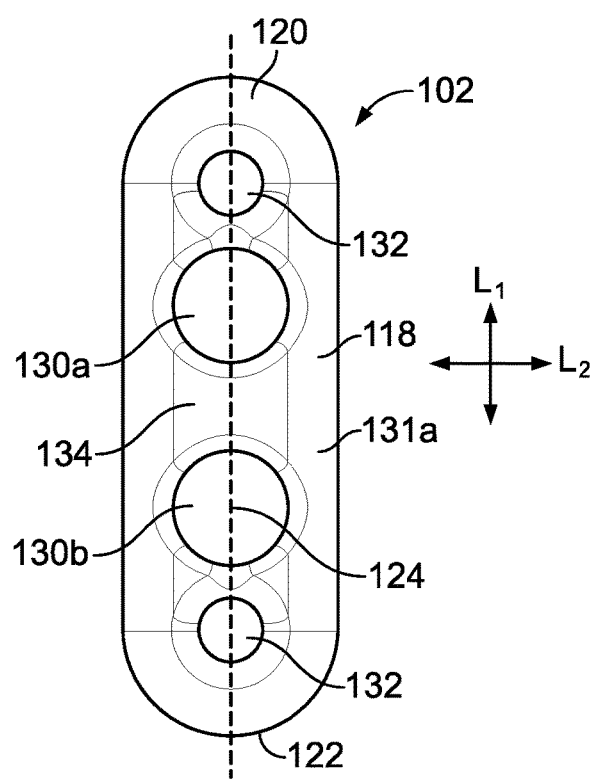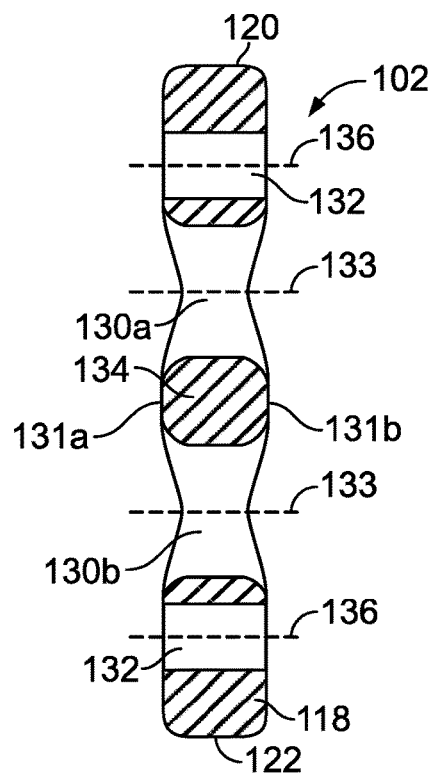
FIG. 3A  FIG. 3B
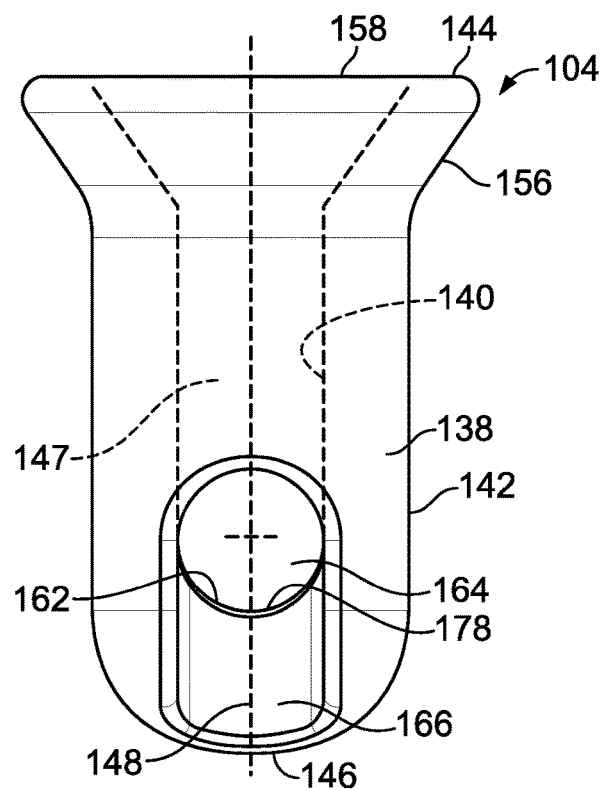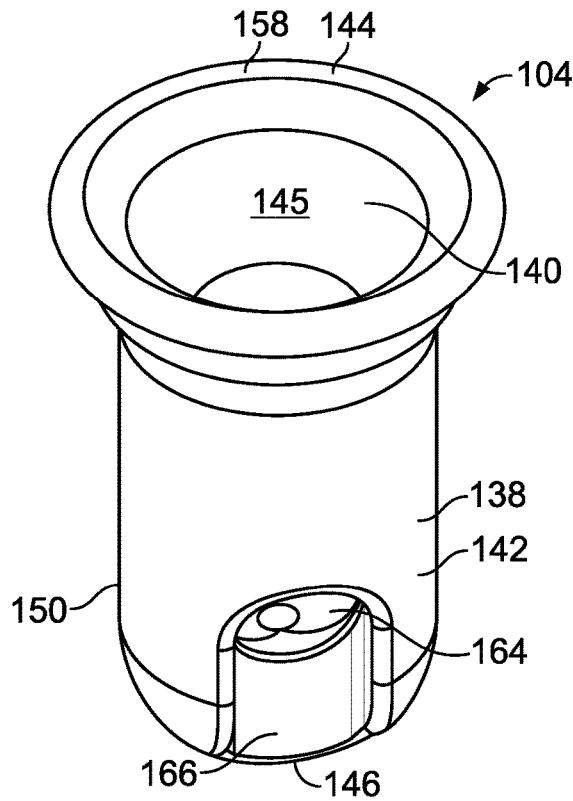
FIG. 4A  FIG. 4B

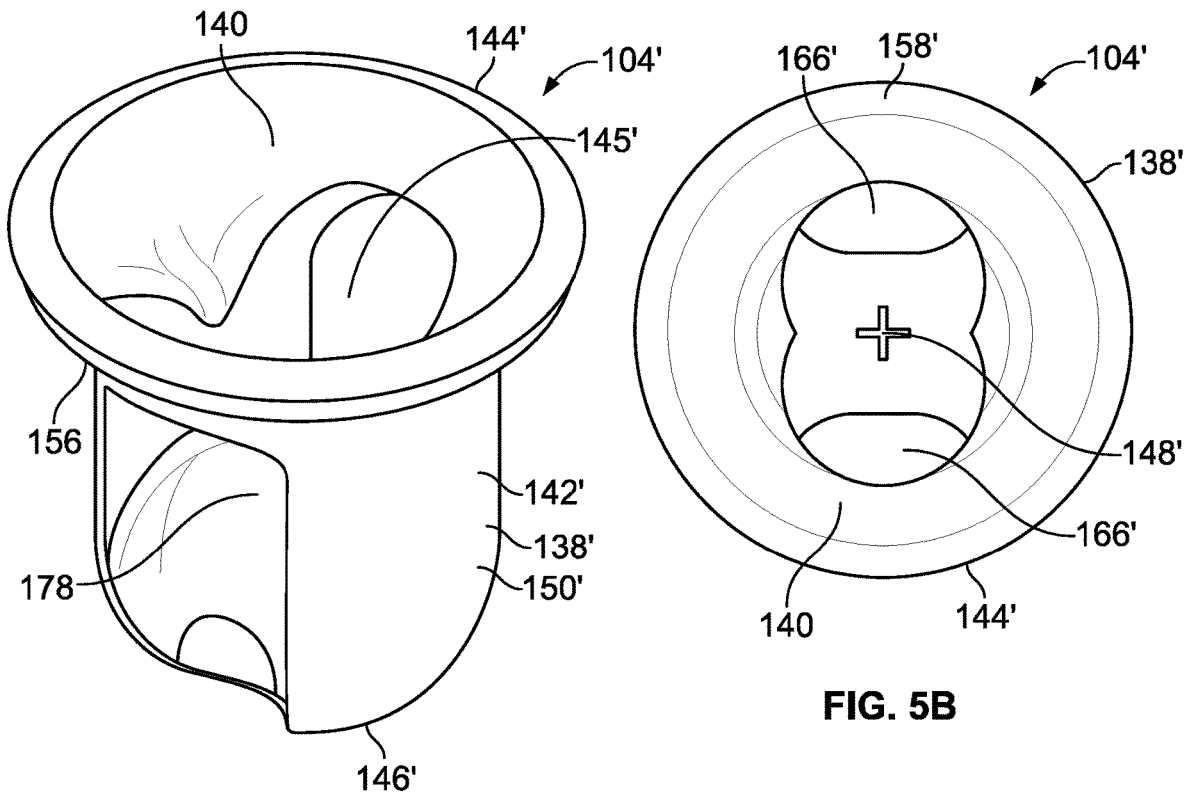
FIG. 5A
FIG. 5B
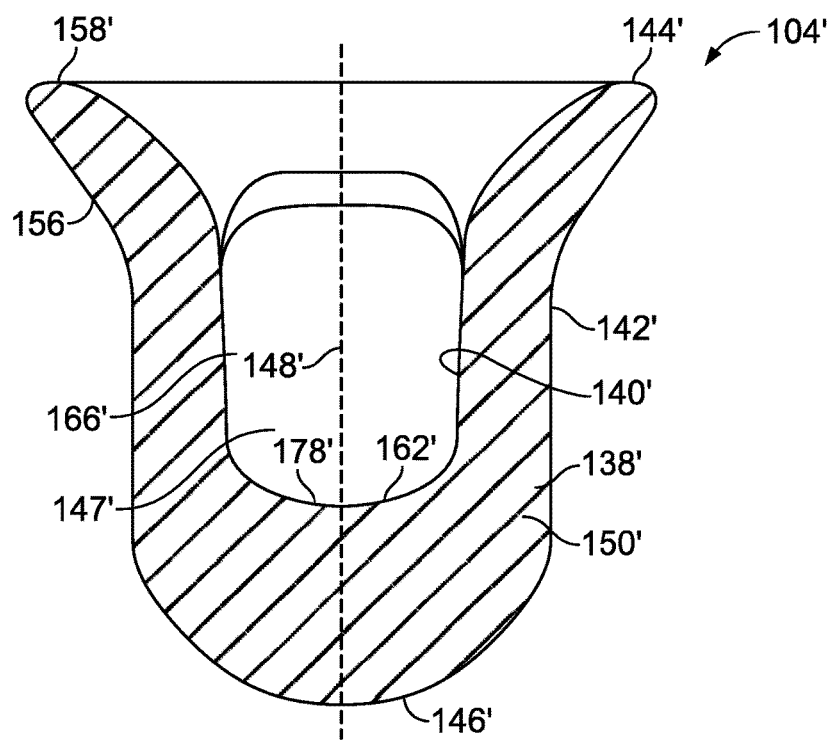
FIG. 5C

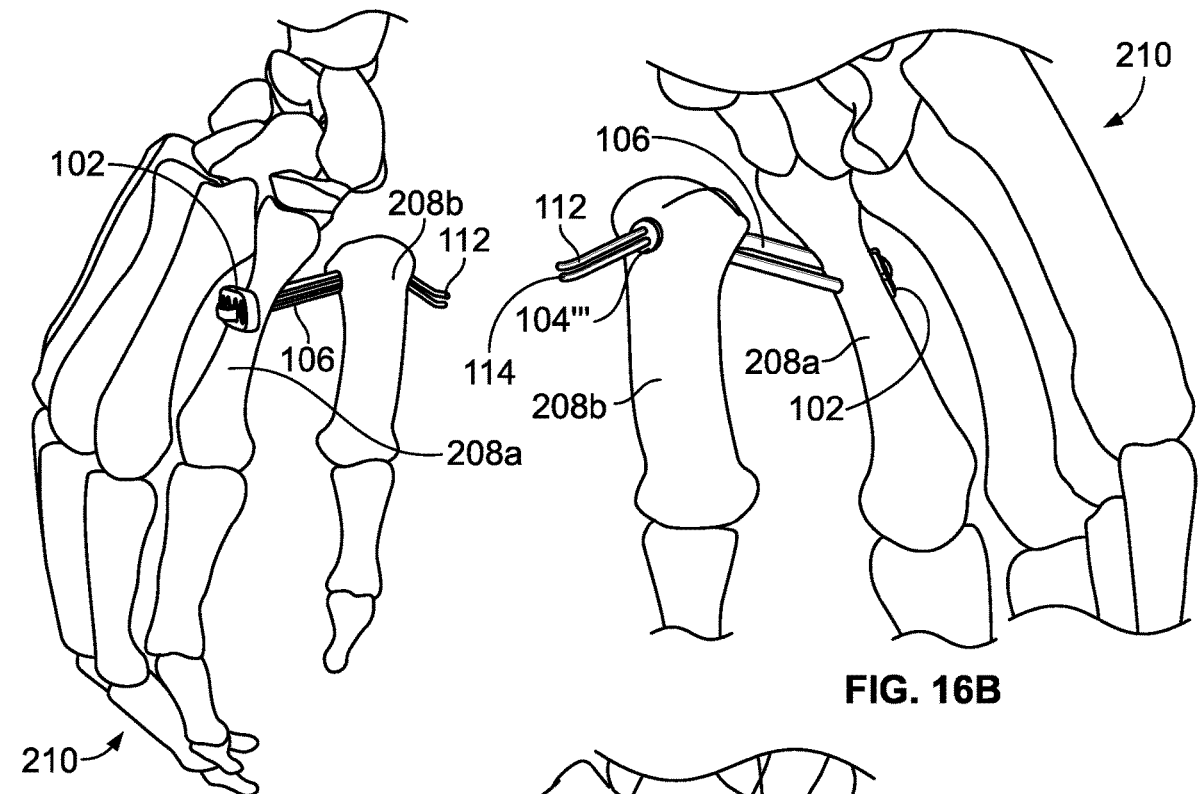
FIG. 16B
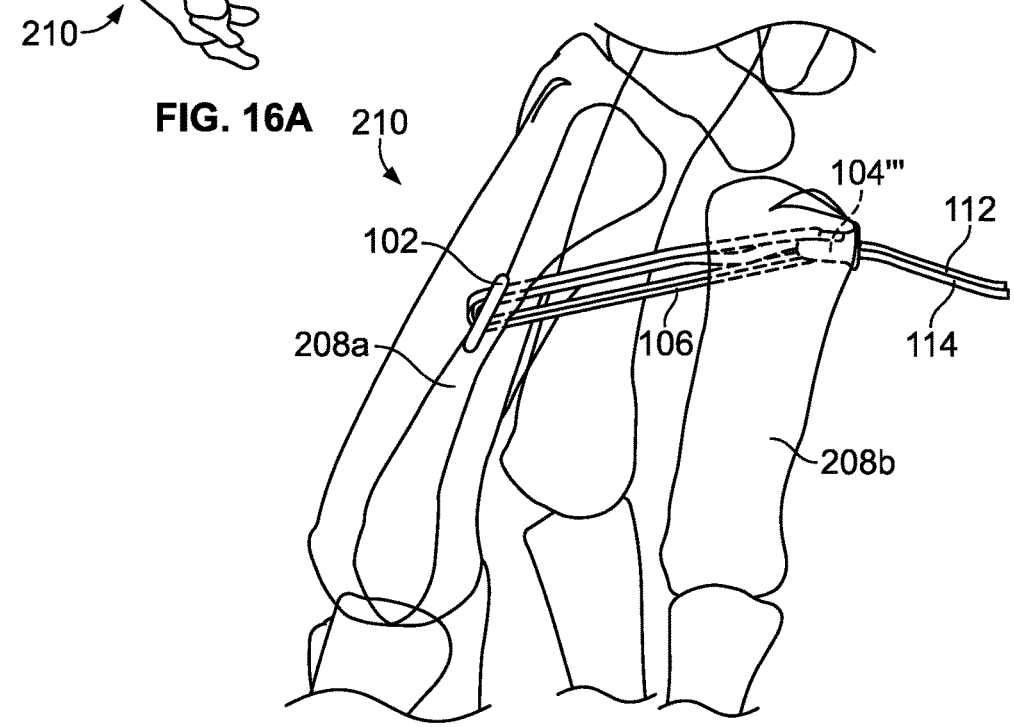
FIG. 16A
FIG. 16C

APPARATUS AND METHOD FOR JOINT REPAIR

CROSS REFERENCE TO RELATED APPLICATIONS

The present application is a continuation of U.S. patent application Ser. No. 16/255,248 filed Jan. 23, 2019 and issued as U.S. Pat. No. 11,045,233, which is a continuation of U.S. patent application Ser. No. 15/764,638 filed Mar. 29, 2018 and issued as U.S. Pat. No. 10,779,868, which is a U.S. National Phase of International PCT Application No. PCT/US2016/055116 filed Oct. 3, 2016, which claims the benefit of U.S. Provisional Patent Application Ser. No. 62/238,845 filed Oct. 8, 2015, the contents of each application hereby incorporated by reference in their entirety.

BACKGROUND

Embodiments of the present invention generally relate to joint repair. More particularly, but not exclusively, embodiments of the present invention relate to an adjustable apparatus that at least assists in maintaining tension on a one or more bones during joint repair and/or healing.

Reconstructive surgery can be utilized to repair damaged and/or unstable sprains, among other injuries. For example, in at least certain instances, reconstructive surgery can be utilized to repair damage to the distal tibiofibular joint, including but not limited to damage associated with certain high ankle sprains and/or breaks and fractures of the fibula and tibia, among repairs to other joints. Such surgeries can seek to establish/re-establish the correct apposition, placement, and/or separation of the fibula relative to the tibia, or vice versa. Further, such reconstructive surgery can also seek to re-establish the integrity of the fibula and tibia, as well as re-establish axial, rotational and transitional forces. A common procedure for repairing certain types of injuries to the distal tibiofibular joint is syndemosis screw fixation. During syndemosis screw fixation, at least two fixation screws are driven into drilled holes in the bone(s) of a patient. Such screws are typically also driven through holes in a bone plate that abuts, or is generally positioned adjacent to, an outer surface of the patient's bone. Yet, such drilling and screw implantation can cause damage to the bone(s) and/or weaken portions of the bone. Further, after several weeks or months of recovery, such hardware is typically removed from the patient, which typically involves the patient undergoing a subsequent or additional procedure.

SUMMARY

Certain embodiments of the present invention provide an apparatus that includes an adjustable tether having a pre-tied knot slideably displaceable in one direction from a first axial position to a second axial position. The apparatus also includes a first bolster device that is coupled to the adjustable tether, the first bolster device having a width and a length that are each sized to accommodate passage of the first bolster device through a passageway in a first orientation of the first bolster device, and which are sized to prevent passage through the passageway when the first bolster device is in a second orientation. Further, the pre-tied knot is tied prior to insertion of the first bolster device into the passageway. The apparatus also includes a second bolster device coupled to the adjustable tether, the second bolster device being positioned between the pre-tied knot and the first bolster device. The second bolster device includes a channel that extends through at least a portion of the second bolster device, the channel being sized to receive placement of the pre-tied knot. Further, an axial distance between the pre-tied knot and the first bolster device is reduced by slideable displacement of the pre-tied knot from the first axial position to the second axial position.

Additionally, certain embodiments of the present invention provide an apparatus comprising a first bolster device and a second bolster device, the second bolster device having a plate portion and a body portion, the body portion including a channel that extends through the plate portion. The apparatus can further include an adjustable tether that extends through one or more apertures of the first bolster device and the body portion of the second bolster device. The adjustable tether includes a pre-tied slideable locking knot that is embedded within the second bolster device. The pre-tied slideable locking knot is displaceable from at least a first position to a second position along the adjustable tether. Additionally, the adjustable tether can have a first length between the first and second bolster devices when the pre-tied slideable locking knot is at the first position and a second length when the pre-tied slideable locking knot is at the second position, the second length being smaller than the first length. Additionally, the pre-tied slideable locking knot is at the first position prior to insertion of the first bolster device into the formed passageway.

Further, certain embodiments include is a method that includes forming, with at least a drill bit, a passageway through one or more bones and disconnecting the drill bit from a drill. Further, a lead suture is coupled to the disconnected drill bit, the lead suture also being coupled to a first bolster device that is coupled to a second bolster device by an adjustable tether that has a pre-tied knot that is embedded at a first position along the adjustable tether within the second bolster device. The lead suture and the first bolster device are displaced through the passageway via displacement of the drill bit. After displacing the first bolster device through the passageway, the pre-tied knot is slid along the adjustable tether from the first position to a second position, with a length of the adjustable tether between the first bolster device and the pre-tied knot being reduced as the pre-tied knot is slid from the first position to the second position.

BRIEF DESCRIPTION OF THE DRAWINGS

The description herein makes reference to the accompanying figures wherein like reference numerals refer to like parts throughout the several views.

FIG. 1A illustrates a side perspective view of a portion of a bolster system that is coupled to a lead suture.

FIG. 1B illustrates a side perspective view of a bolster system that is coupled to a lead suture and which includes an adjustable tether having a pre-tied slideable locking knot.

FIGS. 3A and 3B illustrate a front view and a side cross-sectional view, respectively, of an exemplary embodiment of a first bolster device.

FIGS. 4A and 4B illustrate a front view and top perspective view, respectively, of an exemplary embodiment of a second bolster device.

FIGS. 5A-5C illustrate a front view, a top view, and a side cross-sectional view, respectively, of an exemplary embodiment of a second bolster device.

FIGS. 16A and 16B illustrate an anterior view and a posterior view, respectively, of a bolster system operably extending through adjacent metacarpal bones.

FIG. 16C illustrates a phantom medial view of the bolster system and metacarpal bones shown in FIGS. 16A and 16B.

Figure 2:
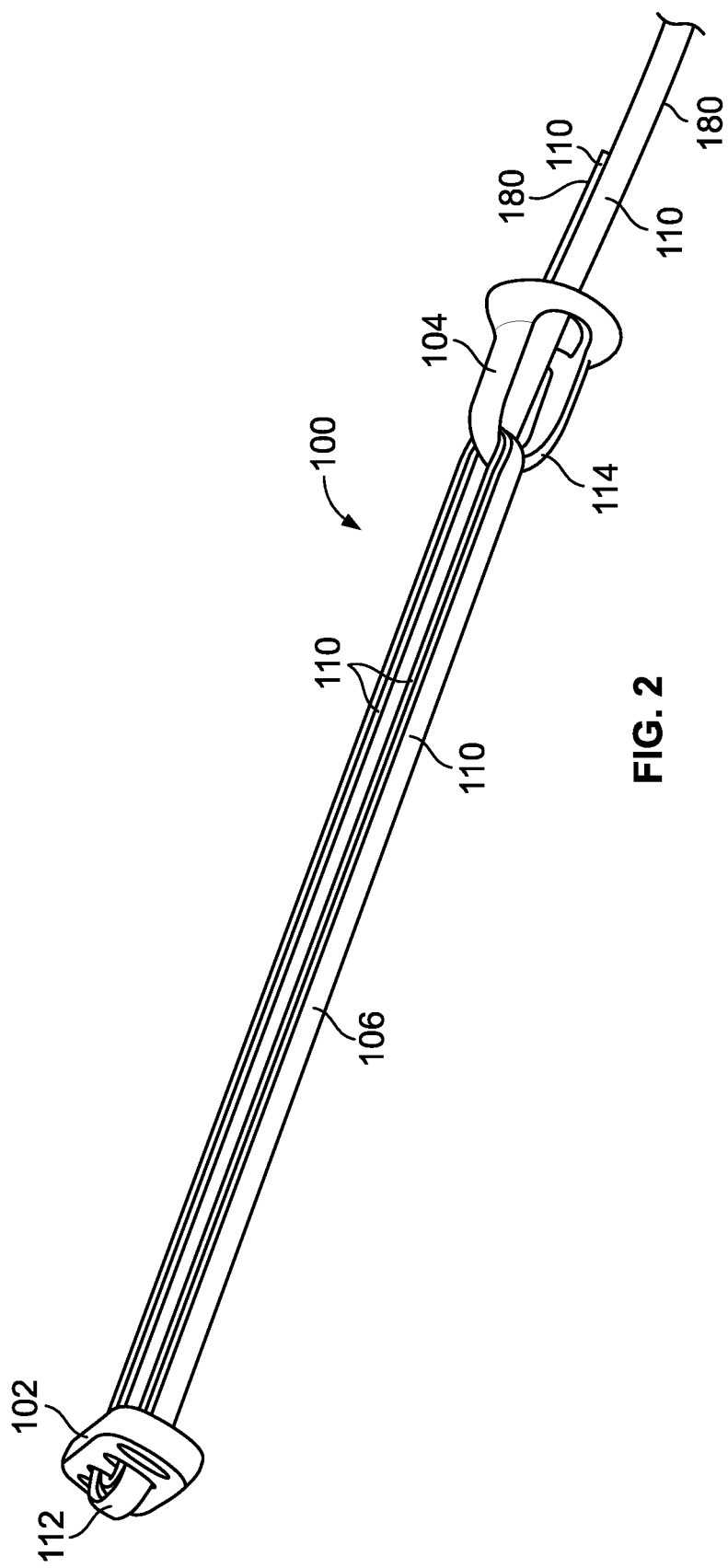
FIG. 2 illustrates a side perspective view of a bolster system.

The foregoing summary, as well as the following detailed description of certain embodiments of the present invention, will be better understood when read in conjunction with the appended drawings. For the purpose of illustrating the invention, there is shown in the drawings certain embodiments. It should be understood, however, that the present invention is not limited to the arrangements and instrumentalities shown in the attached drawings.

DESCRIPTION OF THE ILLUSTRATED EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

FIGS. 1A, 1B and 2 illustrate side perspective views of at least a portion of a bolster system 100 according to an embodiment of the present invention. As illustrated, the bolster system 100 can include a first bolster device 102, a second bolster device 104, and an adjustable tether 106. FIGS. 1A, 1B and 2 further depict a lead suture 108 coupled to the first bolster device 102. The first and second bolster devices 102, 104 can be constructed from a variety of different materials including, for example, stainless steel, plastic and titanium, among other suitable materials. As discussed below in greater detail, the adjustable tether 106 can comprise a wire, fiber or suture 110, among other items or devices, that passes around, through, and/or about at least a portion of the first and second bolster devices 102, 104 so as form an adjustable tether 106 therebetween that is operably coupled to the first and second bolster devices 102, 104. Further, as shown in at least FIGS. 1B and 2, the first bolster device 102 can be positioned at a first end 112 of the adjustable tether 106, while the second bolster device 104 can be positioned at or around a second, opposite end 114 of the adjustable tether 106.

Figure 15A:
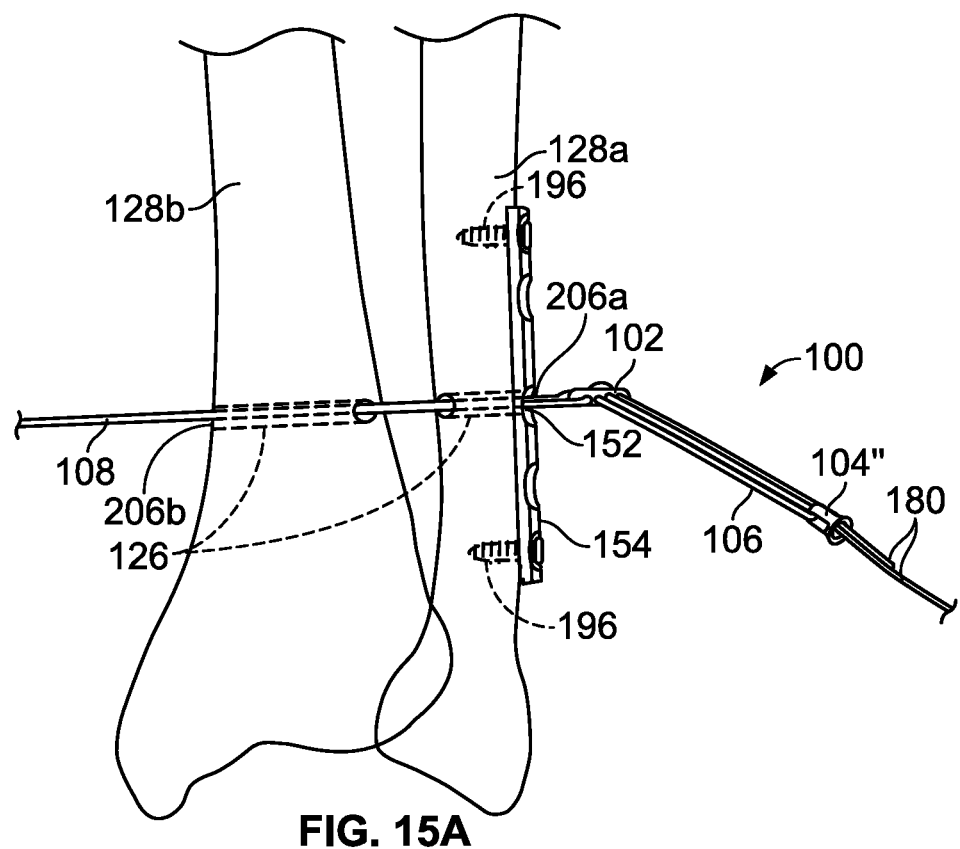
FIG. 15A illustrates an example of a lead suture that is coupled to a bolster system being pulled through a passageway in one or more bones.
Figure 15B:
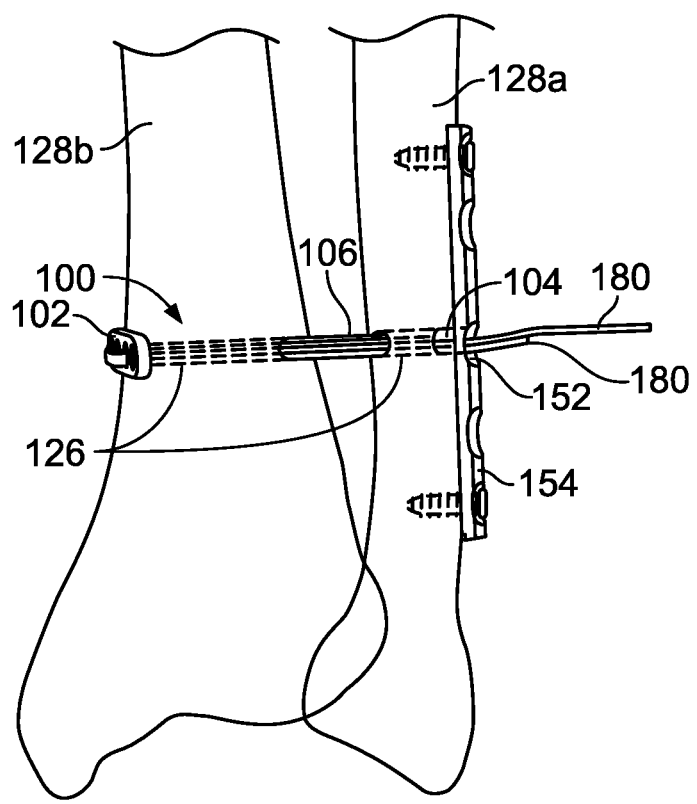
FIG. 15B illustrates an example of a bolster system that is operably positioned to maintain tension on a tibia and femoral bone in connection with syndemosis joint repair.

As illustrated in at least FIG. 1B, and as discussed below in greater detail, the adjustable tether 106 can include a pre-tied slideable locking knot 116 at or around the second end 114 of the adjustable tether 106. Moreover, according to the illustrated embodiment, the slideable locking knot 116 can be positioned at an end of the tether 106 adjacent to the second bolster device 104. The pre-tied slideable locking knot 116 can be structured for use in adjusting a length of the adjustable tether 106 between the first and second bolster devices 102, 104 and/or to secure relative positions of the first and second bolster devices 102, 104 so that the bolster system 100 at least provides tension on a fibula and tibia bones 128a, 128b (FIG. 15B). Further, according to certain embodiments, the slideable locking knot 116 can be a one-way locking knot, and more specifically a knot that can shorten, but not expand, at least the distance of the locking knot 116 from the first bolster device 102 relative to the adjustable tether 106. A variety of different types of knots can be used as the pre-tied slideable locking knot 116 including, but not limited to, a woven, fast fix, square, and cow hitch knot, among other suitable types and styles of knots.

As illustrated in FIG. 1B, according to certain embodiments, the pre-tied slideable locking knot 116 can comprise lockingly intertwined portions of one or more sutures 110 of the adjustable tether 106 that extend away from the second bolster device 104. Further, according to the illustrated embodiment, the pre-tied slideable locking knot 116 is formed prior to implantation of at least a portion of the bolster system 100 into one or more bones of a patient. For example, FIG. 1B provides an indication of the routing of portions of the suture 110 about itself or other sutures 110 in a manner that can form the pre-tied slideable locking knot 116 prior to implantation of the bolster system 100 into a patient. Additionally, as discussed below, the pre-tied slideable locking knot 116 can be formed in a manner that allows the pre-tied slideable locking knot 116 to be displaced along at least a portion of the adjustable tether 106, at least after a portion of the bolster system 100 has routed through a passageway in a bone 128a, 128b of a patient in a manner that can facilitate or enhance the ability of the bolster system 100 to exert compressive tension against one or more of the patient's bones 128a, 128b.

Additionally, according to certain embodiments, the tether 106 can extend from the second bolster device 106 to first bolster device 102, where a portion of the tether 106 can wrap or extend around a portion of the first bolster device 102, and return to the second bolster device 104, where a portion of the tether 106 can wrap or extend around a portion of the second bolster device 104. According to certain embodiments, this process can be repeated one or more additional times in a manner that accommodates multiple portions or loops of the tether 106 being wound and/or extending between the first and second bolster devices 102, 104. Further, opposing ends of the tether 106 can extend from the second bolster device 104 such that at least a portion of the tether 106 forms the slideable locking knot 116.

FIGS. 3A and 3B illustrate front and side cross-sectional views, respectively, of an exemplary embodiment of a first bolster device 102. As illustrated, the first bolster device 102 can include a body portion 118 that extends between first and second ends 120, 122 along a central axis 124. Further, according to the illustrated embodiment, the first bolster device 102 can have a first length or height in a direction that is relatively or generally parallel to the central axis 124 (as indicated by the "L1" direction in FIG. 3A) that is longer than a second length or width of the first bolster device 102 in a direction that is arranged generally perpendicular to the central axis 124 (as indicated by the "L2" direction in FIG. 3A). For example, according to certain embodiments, the first bolster device 102 can have a variety of shapes including, for example, rectangular, trapezoidal, oval, or triangular, among other suitable shapes and sizes. As discussed below in greater detail, according to certain embodiments, such a configuration can permit the first bolster device 102 to be manipulated to a first orientation in which the first bolster device 102 can pass through a passageway 126 in one or more bones 128 a, 128 b (FIGS. 15A and 15B) that has a size that is similar or greater than the second length or width of the first bolster device 102, but which is less than the first length of the first bolster device 102. Upon removal from the passageway 126, the first bolster device 102 can be placed in a second orientation in which the first bolster device 102 is positioned in a manner that utilizes the larger first length of the first bolster device 102 to prevent re-entry of the first bolster device 102 into the passageway 126.

According to the illustrated embodiment, the first bolster device 102 includes one or more tether apertures 130a, 130b that extend between the front side 131a and the back side 131b of the first bolster device 102 along an aperture axis 133 that can be arranged generally perpendicular to the central axis 124 of the first bolster device 102. The tether apertures 130a, 130b are sized to at least receive one or more passages of portions of the suture(s) 110 of the adjustable tether 106. For example, according to the illustrated embodiment, the first bolster device 102 includes a first tether aperture 130a and a second tether aperture 130a, the first and second tether apertures 130a, 130b being separated from one another by a bridge portion 134 of the first bolster device 102. According to such embodiment, at least a portion of the suture 110 can extend in a first direction generally away from the second bolster device 104 through one of the first and second tether apertures 130a, 130b of the first bolster device 102, and subsequently pass through the other of the first and second tether apertures 130a, 130b in a second, opposite direction generally toward the second bolster device 104. Such passages of the suture 110 through the first and second tether apertures 130a, 130b can be repeated one or more times. Additionally, according to certain embodiments, at least a portion of the suture 110 can also be wrapped through the first and second tether apertures 130a, 130b and around the bridge portion 134 of the first bolster device 102. Alternatively, according to other embodiments, the sutures 110 can pass through one of the first and second tether apertures 130a, 130b before returning back toward the second bolster device 104. Further, according to certain embodiments, the adjustable tether 106 can comprise separate sutures 110 that each extend through separate ones of the tether apertures 130a, 130b, and which are joined together by the pre-tied slideable locking knot 116.

According to certain embodiments, the first bolster device 102 can also include one or more lead suture apertures 132 that extend between the front side 131a and the back side 131b of the first bolster device 102 along an aperture axis 136 that can be generally arranged perpendicular to the central axis 124 of the first bolster device 102. The lead suture apertures 132 can be sized to at least accommodate the passage of a lead suture 108 (FIG. 1A) that can be used in the displacement of the first bolster device 102 through a passageway 126 in one or more bones 128a, 128b, as discussed in greater detail below. According to the illustrated embodiment, the first bolster device 102 is depicted as having two lead suture apertures 132. However, according to certain embodiments, the lead suture 108 may extend through only one of the lead suture apertures 132. Additionally, according to certain embodiments, the first bolster device 102 can have only one lead suture aperture 132 through which the lead suture 108 extends. Further, the lead suture aperture 132 may, or may not, be configured as an aperture that is separate from the tether apertures 130a, 130b such that lead suture 108 and the suture 110 of the adjustable tether 106 do, or do not, extend through the same aperture. Further, while FIGS. 1A and 2 illustrate the lead suture apertures 132 positioned outside of the tether apertures 130a, 130b, according to other embodiments, the tether apertures 130a, 130b can be positioned outside of the lead suture apertures 132 such that the tether apertures 130a, 130b are separated from each other by one or more of the lead suture apertures 132.

FIGS. 4A and 4B illustrate front and top perspective views, respectively, of an exemplary embodiment of a second bolster device 104. According to the depicted embodiment, the second bolster device 104 includes a wall 138 having an inner portion 140, an outer portion 142, a first end 144, and a second end 146. According to certain embodiments, the wall 138 extends from the first end 144 to the second end 146 of the wall 138 of the second bolster device 104 along a central axis 148. Further, at least a portion of the wall 138 is configured to provide a generally elongated body portion 150. The body portion 150 can have a variety of different shapes and sizes, such as, for example, having an oval, square, rectangular, or other non-circular cross-sectional shapes, among other suitable shapes. According to the illustrated embodiment, the body portion 150 is generally cylindrical such that the second bolster device 104 can have a plug shape. Further, the body portion 150 can be sized such that at least a portion of the body portion 150 extends into a passageway 126 formed in a bone(s) 128a, 128b and/or through an aperture 152 in a bone plate 154 (FIGS. 10A and 10B), as discussed in greater detail below.

According to certain embodiments, the wall 138 can also include a tapered portion 156 in which the wall 138 outwardly extends from the elongated body portion 150 to a plate portion 158 at the first end 144 of the wall 138. For example, in the illustrated embodiment, the wall 138 can have a size such as, for example, a diameter, along the elongated body portion 150 of the second bolster device 104 that is smaller than a corresponding size, such as a diameter of the plate portion 158 at the first end 144 of the wall 138. According to certain embodiments, at least a portion of the outer portion 142 of the wall 138 along the tapered portion 156 and/or plate portion 158 can be sized to prevent the entire second bolster device 104 from being pushed or pulled into the passageway 126 in one or more bones 128a, 128b and/or through an aperture 152 in a bone plate 154. For example, at least the plate portion 158 can have a size that abuts against an adjacent portion of bone or an inner wall of an aperture 152 in a bone plate 154 while at least a portion of the body portion 150 extends into the passageway 126 and/or through the aperture in the bone plate 154. Further, the second bolster device 104 can be sized to prevent the second bolster device 104, such as the first end of the second bolster device 104, from extending beyond an outer surface 153 of the bone plate 154 when the second bolster device 104 is operably positioned in the aperture 152 of the bone plate 154.

Additionally, according to certain embodiments, at least a portion of the elongated body portion 150 can be provided with a shape and/or size that assists in the positioning of at least a portion of the body portion 150 of the second bolster device 104 in the passageway 126 in a bone(s) 128a, 128b and/or through an aperture 152 of a bone plate 154. For example, as shown in at least FIG. 4A, according to certain embodiments, the elongated body portion 150 can decrease in size as the wall 138 approaches the second end 146 of the wall 138 of the second bolster device 104. For example, according to certain embodiments, the elongated body portion 150 can taper inwardly and/or have a chamfer or curvature as the wall 138 approaches the second end 146, as shown in at least FIG. 4A.

The first end 144 of the wall 138 of the second bolster device 104 can include an inlet 145 in communication with a channel 147 that extends within a portion of the second bolster device 104 along the central axis 148. For example, according to certain embodiments, the channel 147 can extend from the inlet 145 to an opposite base portion 162 of the channel 147. Further, the inlet 145 and the base portion 162 can be separated from each other by a distance that provides the channel 147 with a depth that can accommodate the recessed insertion or embedding of the pre-tied slideable locking knot 116 of the adjustable tether 106 into/in the channel 147, as discussed in greater detail below. More specifically, the depth of the channel 147 can allow the pre-tied slideable locking knot 116 to be placed in the channel 147 in a manner that prevents the pre-tied slideable locking knot 116 from extending beyond the inlet 145, and thereby be recessed or embedded in the channel 147 below at least a portion of the plate portion 158 of the second bolster device 104.

According to certain embodiments, the second bolster device 104 can include one or more tether openings 164 and/or recesses 166 that are in communication with the channel 147. While certain embodiments the second bolster device 104 illustrated herein are depicted as having two tether openings 164, the number of tether openings 164 can vary, including, but not limited to, having a single tether opening 164 or three or more tether openings 164. According to the embodiment illustrated in FIGS. 4A and 4B, recesses 166 on opposing sides of the wall 138 can generally extend upwardly from the second end 146 of the second bolster device 104 to a tether opening 164 in the body portion 150 of the wall 138. Moreover, the recesses 166 may be positioned so as to extend from at least a portion of the second end 146 of the second bolster device 104 to different or opposing sides of the channel 147. Further, the recesses 166 can extend into the wall 138 at a depth that may permit the adjustable tether 106 to be recessed in the recess 166 such that adjustable tether 106 does not outwardly protrude from the recess 166 beyond the outer portion 142 of the wall 138. Alternatively, the recesses 166 can have a depth to accommodate portions of the adjustable tether being compressed into the recesses 166 when the body portion 150 is positioned in a passageway 126. Thus, according to certain embodiments, at least when the bolster system 100 is operably implanted in a patient, the portion of the adjustable tether 106 positioned along and/or within the recesses 166 can generally be arranged flush with or recessed below adjacent outer portions 142 of the wall 138 so that the recessed portions of the adjustable tether 106 are not in a position that interferes with the placement of at least a portion of the second bolster device 104 in the passageway of a bone 128a, 128b and/or an aperture 152 of a bone plate 154.

According to the illustrated embodiment, a tether opening 164 can extend through opposing sides of the wall 138 along an axis 168 that is arranged generally perpendicular to the central axis 148 of the second bolster device 104. According to certain embodiments, the tether opening 164 may be formed by an intersection of the channel 147 with the recesses 166, and can also define the location of the base portion 162. For example, according to the embodiment shown in FIGS. 4A and 4B, the tether opening 164 can be positioned such that one or more sutures 110 of the adjustable tether 106 can extend in a direction that is generally directed away from the first bolster device 102 along one of two recesses 166 in the sidewall 138 before extending across a bridge portion 178 at the base portion 162 of the channel 147, and subsequently extend along the other of the two recesses 166 in the sidewall 138 in a direction that is generally directed toward the first bolster device 102. Thus, according to such an embodiment, the wall 138 can have a thickness between the base portion 162 of the channel 147 and the second end 146 that can accommodate forces exerted on the bridge portion 178 of the second bolster device 104 by the adjustable tether 106.

FIGS. 5A-5C illustrate front, top, and side cross-sectional views, respectively, of an exemplary embodiment of a second bolster device 104'. As illustrated in FIGS. 5A-5C, according to the illustrated embodiment, a pair of opposing recesses 166' extend upwardly generally from the second end 146' of the wall 138' to an area at or around the tapered portion 156' of the wall 138'. Additionally, at least a portion of the recesses 166' extend to a depth in the wall 138' that exposes a portion of the channel 147', or otherwise allows the recesses 166' to be positioned in communication with the channel 147'. Further, the recesses 166' and/or base portion 162' of the channel 147' can have a rounded or chamfered shape so as to prevent the adjustable tether 106' from transitioning from the recesses 166' to the bridge portion 178 at the base portion 162' along a corner or sharp edge.

Figure 6A:
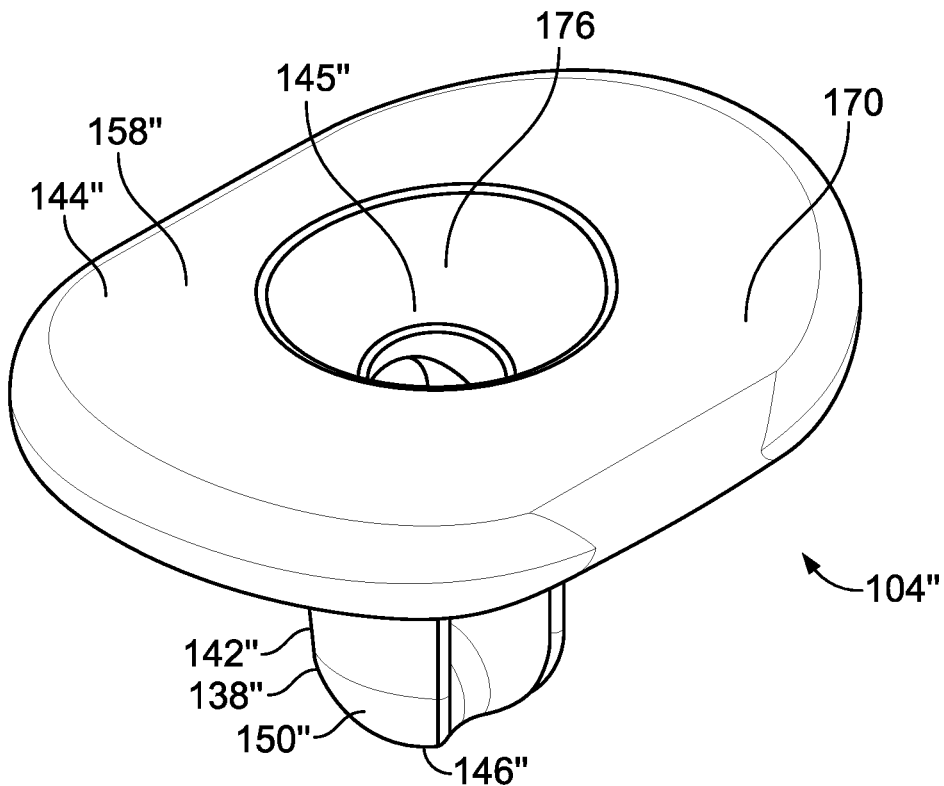
FIGS. 6A and 6B illustrate a front view and top view, respectively, of an exemplary embodiment of a second bolster device.
Figure 6B:
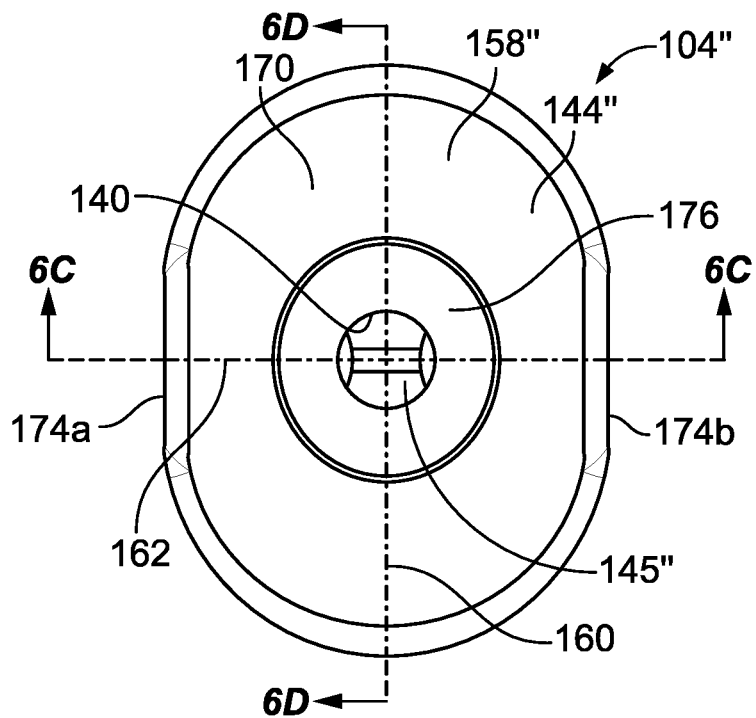
Figure 6C:
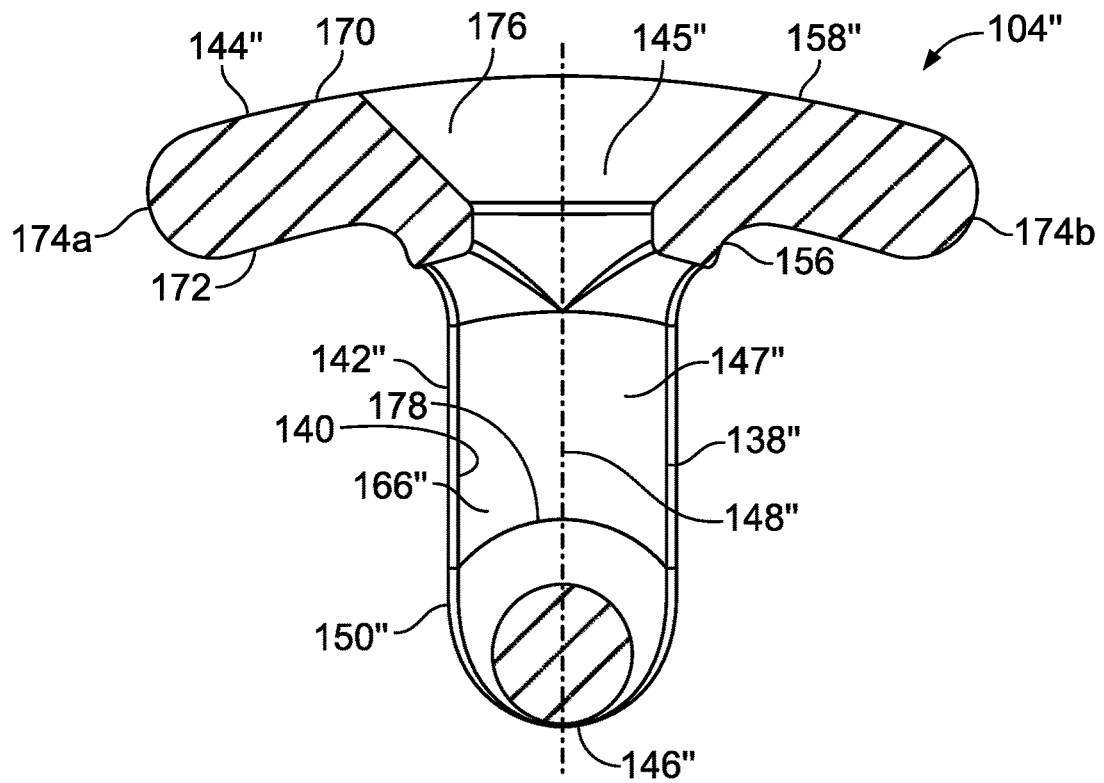
FIG. 6C illustrates a cross-sectional view of an embodiment of a second bolster device taken along line 6C-6C of FIG. 6B.
Figure 6D:
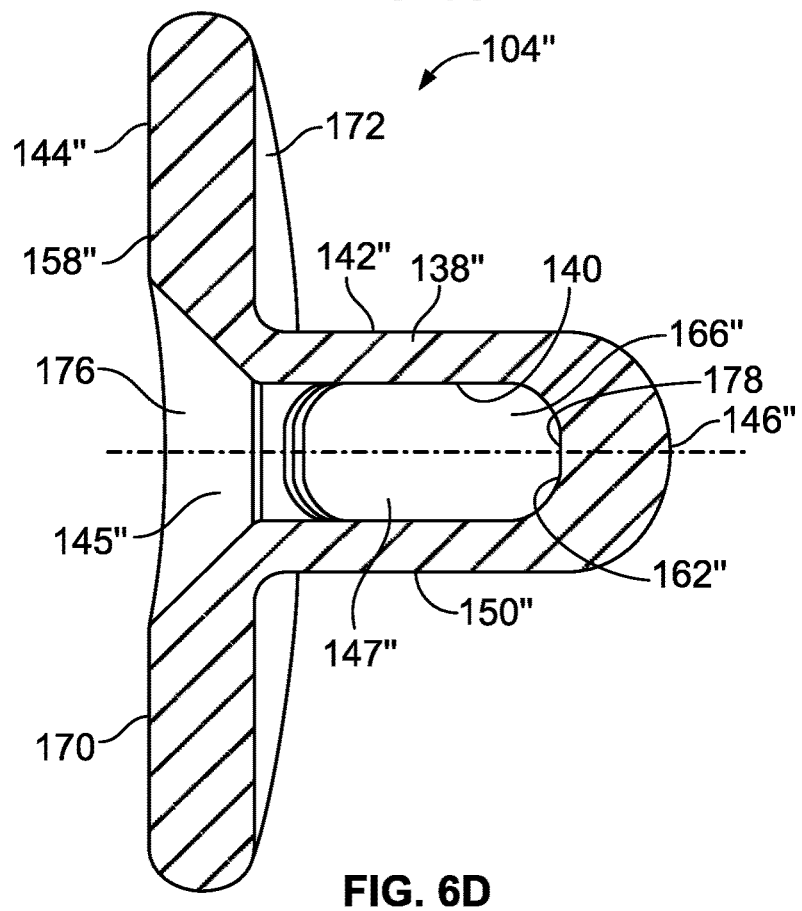
FIG. 6D illustrates a cross-sectional view of an exemplary embodiment of a second bolster device taken along line 6D-6D of FIG. 6B.

FIGS. 6A-6D illustrate front and top views, respectively, of an exemplary embodiment of a second bolster device 104". As illustrated in FIGS. 6A-6C, the plate portion 158" can extend from the body portion 150" in a direction that is arranged generally perpendicular to the channel 147" and/or the body portion 150". Further, the plate portion 158" can have an oversized and/or generally elongated shape. For example, according to certain embodiments, the plate portion 158" can have a length along a first axis 160 (which is shown as shared by line 6D-6D in FIG. 6B) of the plate portion 158" arranged generally perpendicular to the central axis 148" that is at least equal to, if not longer, than a length or width along a second axis 160 (which is shown as shared by line 6C-6C in FIG. 6B) that extends in a direction arranged generally perpendicular to the first axis 160. For example, according to certain embodiments, the plate portion 158" can have a length along the first axis 160 that is at least about 1 to around 3 times larger, and more particularly about 1.1 to about 1.5 times larger, than the length of the plate portion 158" along a second axis 160. Additionally, according to certain embodiments, the length of the plate portion 158" along the first axis 160 can be approximately one-half inch (½") while the length of the plate portion 158" along a second axis 160 can be approximately three-eighths of an inch (⅜").

Figure 8:
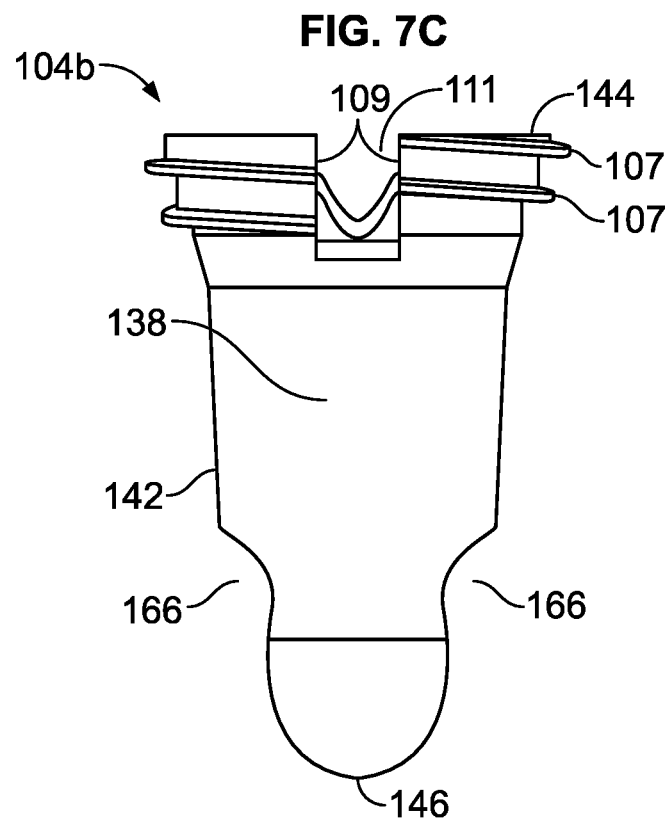
FIG. 8 illustrates a side view of an exemplary embodiment of a second bolster device having a threaded member.

The elongated shape of the plate portion 158", and moreover the elongated shape of the plate portion 158" along at least the first axis 160, can, in at least certain circumstances, eliminate the need, whether actual or perceived, for the inclusion of a bone plate 154 (FIG. 8). Further, by eliminating the use of a bone plate 154 in at least certain circumstances, the step of drilling holes into bone 128a, 128b and implanting screws into those drilled holes to secure the bone plate 154 to bone 128a can also be eliminated, as well as the associated risks and damage such holes and screws can present to the bone 128a. Further, such an elongated shape can provide a relatively wide area for the plate portion 158" to abut and/or press against the adjacent bone 128a. Moreover, by providing a large area in which the plate portion 158" abuts against the bone 128a, forces exerted onto the bone 128a by the plate portion 158" can be distributed over a larger area. By distributing the forces exerted onto the bone 128a by the plate portion 158" over a larger area, the plate portion 158" of the present design can have a decreased likelihood of breaking through the cortex of the bone 128a.

According to the embodiment depicted in FIGS. 6A-6D, the length of the plate portion 158" along the first axis 160 can be around the same or greater than the overall length of the second bolster device 104" along the central axis 148". For example, according to certain embodiments, the length of the plate portion 158" along the first axis 160 can be approximately 1.1 to approximately 3 times greater than the overall length of the second bolster device 104" along the central axis 148". As another example, the length of the plate portion 158" along the first axis 160 can be approximately one-half inch (½"), which can be approximately 1.5 to 2 times larger than the overall length of the second bolster device 104" from a top surface 170 of the plate portion 158" to the second end 146" of the wall 138".

According to certain embodiments, the plate portion 158" can be curved in at least one direction. The location, orientation, degree, and number of curvatures can be based on a variety of different factors, including the ability of at least a portion of the bottom surface 172 of the plate portion 158" to be shaped to generally conform to the shape and/or size of the portion of the bone 128a against which at least a portion of the bottom surface 172 can abut. For example, according to the illustrated embodiment, the plate portion 158", including the top and bottom surfaces 170, 172, can be curved between first and second sidewalls 174a, 174b that are on opposite sides of the first axis 160. According to such an embodiment, the apex of the curvature can extend around the first axis 160. Further, such a curvature along the bottom surface 172 of the plate portion 158" can, in at least certain embodiments, facilitate the ability of the bottom surface 172 of the plate portion 158" to be positioned in relatively flush contact with a fibular cortex.

The inlet of the second bolster device 104" can extend through the plate portion 158" such that at least a portion of the adjustable tether 106 can at least initially extend outside of the channel 147" and beyond the plate portion 158" through the inlet 145". Further, in the illustrated embodiment, the plate portion 158" can include a chamfered or inclined inner wall 176 that can facilitate the passage of at least a portion of the adjustable tether 106 such as, for example, the pre-tied slideable locking knot 116, into the channel 147". Further, the body portion 150" of the second bolster device 104" shown in at least FIGS. 6A, 6C and 6D can be configured similar to any of the body portions 150, 150' shown in FIGS. 4A-5C, or can have a variety of other shaped body portions.

Figure 7B:
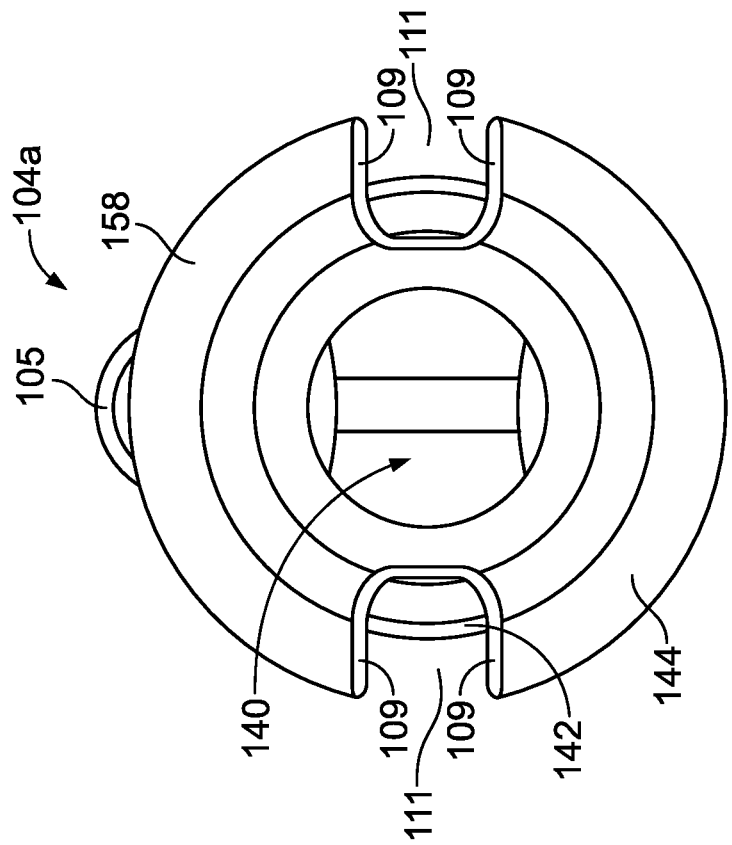
FIGS. 7B and 7C illustrate a top view and a bottom view, respectively, of the second bolster device shown in FIG. 7A.
Figure 7A:
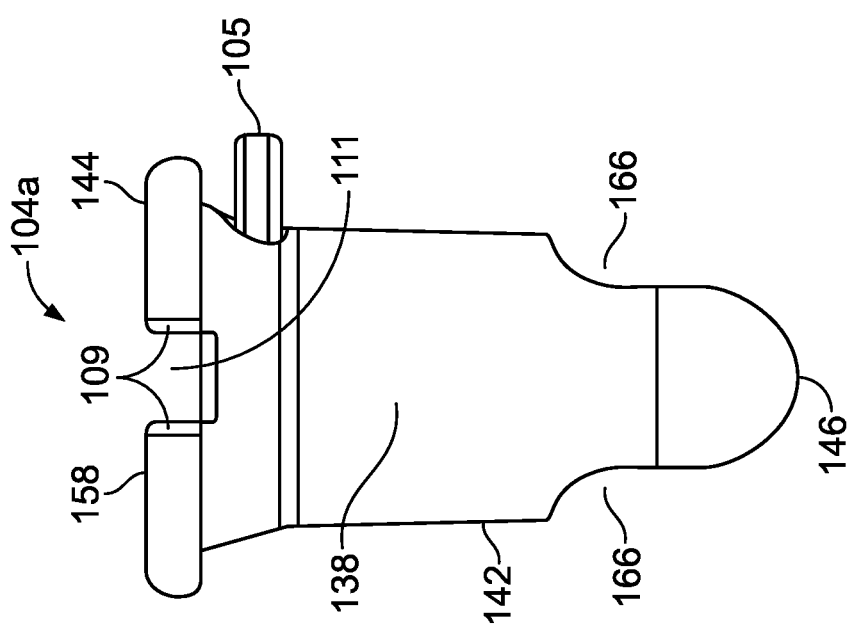
FIG. 7A illustrates a side view of an exemplary embodiment of a second bolster device having a retention tab.
Figure 7C:
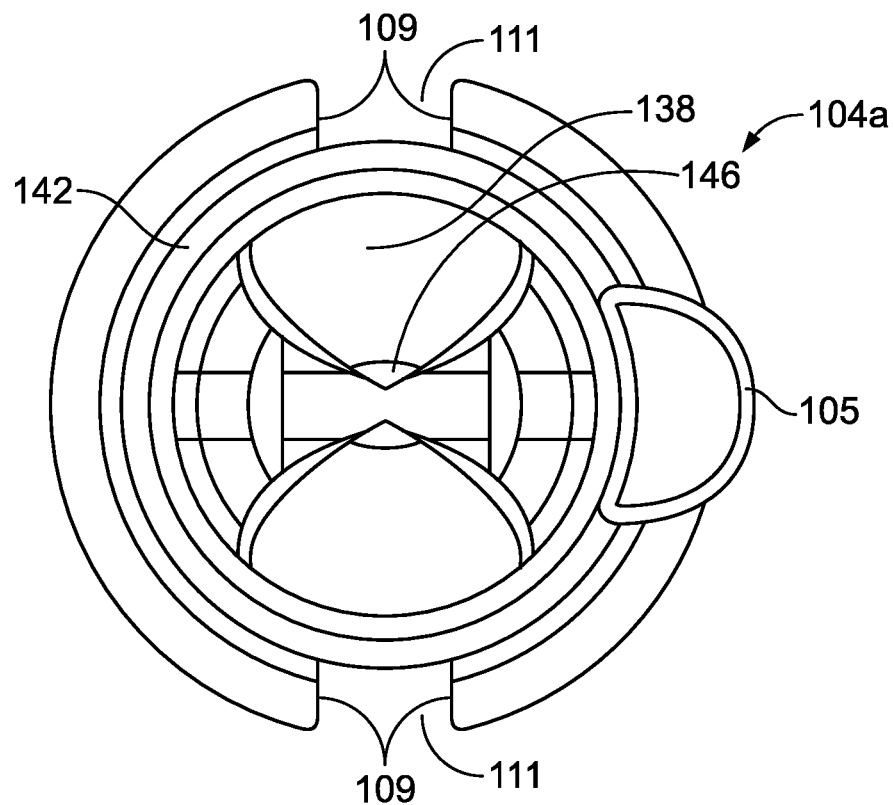

FIGS. 7A-7C illustrate another exemplary embodiment of a second bolster device 104a having one or more retention tabs 105 that outwardly project from the outer portion 142 of the wall 138. The retention tabs 105 can have a variety of shapes and sizes. For example, according to the illustrated embodiment, as shown in FIG. 7A, the retention tab 105 has a generally planar profile and outwardly extends from the wall 138 in a direction that is arranged perpendicular to the central axis 148, 148', 148" (FIGS. 4A, 5C and 6C). Further, as shown in FIGS. 7B and 7C, according to certain embodiments, the retention tab 105 can have a generally round or curved shape. However, it should be understood that the retention tab 105 can have a variety of other shapes or profiles.

The retention tab 105 is positioned and shaped to engage one or more locking lobes or teeth 200 in an aperture 152 of a bone plate 154 (FIGS. 8A and 8B) in a manner that may assist in retaining the second bolster device 104a in locking engagement with the locking teeth 200. For example, according to certain embodiments, the retention tab(s) 105 may be sized to engage a side of the locking tooth/teeth 200 that faces toward the bone of the patient. Moreover, the retention tab 105 can be positioned and sized relative to at least the locking teeth 200 such as when the second bolster device 104a is rotated into an aperture of the bone plate 154, the retention tab 105 can be rotated to a position below the superior plate surface such that the retention tab 105 is generally positioned between the bone and the adjacent locking tooth/teeth 200. For example, according to certain embodiments, the retention tab 105 can be sized to be at displaced through a space or gap between adjacent locking teeth 200 as the second bolster device 104a is rotated relative to the aperture 152 so that the retention tab 105 is positioned beneath at least one locking tooth 200.

With the retention tab 105 at such a position, the locking tooth 200 may be positioned to engage with the retention tab 105 in a manner in which the locking tooth/teeth 200 provides an interference or barrier against at least subsequent axial displacement of the second bolster device 104a out of the associated aperture 152. Such engagement between the retention tab 105 and the one or more locking lobes or teeth 200 in the aperture 152 of the bone plate 154 can, for example, at least assist in retaining the second bolster device 104a in position relative to at least the bone plate 154, including, for example, in instances where the tension on the fractured bones that is provided by use of the bone plate 154 and associated bone screws changes. For example, in at least certain instances in which tension used to hold a position of bones or fractures is reduced, engagement between the retention tab 105 and the one or more locking lobes or teeth 200 can at least assist in preventing the second bolster device 104a from being displaced away from, or at least partially popping out of, the bone plate 154. Additionally, the retention tab 105 and/or locking tooth/teeth 200 may be positioned such that the retention tab 105 is in pressing engagement with the locking tooth/teeth 200, or another force is asserted between the retention tab 105 and locking tooth/teeth 200 that prevents at least rotational displacement of the second bolster device 104a relative to the bone plate 154. For example, according to the embodiment illustrated in FIGS. 7A-7C, the retention tab 105 is positioned at a distance below the plate portion 158 at the first end 144 of the second bolster device 104a at a location in which the tab engages at least a portion of one or more of the locking teeth 200. For example, the retention tab 105 can be positioned about 0.015 millimeters (mm) to about 0.020 millimeters (mm) below the proximately adjacent bottom surface of the plate portion 158 of the second bolster device 104a.

Additionally, the retention tab 105 can outwardly extend to a distance that is greater than a similar outward distance of other relatively adjacent portions of the plate portion 158. For example, according to certain embodiments, the tab portion 105 can outwardly extend approximately 0.09 millimeters (mm) further than the corresponding outward distance of the proximately adjacent portion of the plate portion 158. Further, to at least facilitate such locking engagement, at least one of the retention tabs 105 and the locking tooth/teeth 200 can be configured to be deformed, deflected, or otherwise bent when in a pressed engagement with the other of the retention tab 105 and the locking tooth/teeth 200. For example, according to certain embodiments, the retention tab 105 can have a thickness of approximately 0.020 millimeters (mm).

FIG. 8 illustrates a side view of an exemplary embodiment of a second bolster device 104b having a threaded member 107. According to the illustrated embodiment, the threaded member 107 is configured as an external thread structured to engage one or more of the locking teeth 200 of the bone plate 154 in a manner that at least assists in maintaining the second bolster device 104b in locking engagement with the bone plate 154. Moreover, the thread member 107 can engage one or more of the locking teeth 200 of the bone plate 154 in a manner that at least resists removal of the second bolster device 104b from the bone plate 154. For example, according to the illustrated embodiment, at least a portion of the previously discussed plate portion 158 can include, or be replaced by, the threaded member 107. As the second bolster device 104b is rotated within the aperture 152 of the bone plate 154 and axially displaced toward the bone, at least a portion of the threaded member 107 may pass through a gap or space between adjacent locking teeth 200 of the bone plate 154 and proceed to a position in which at least a portion of the threaded member 107 below the superior surface of the bone plate 154 and between at least one locking tooth 200 and the bone. With at least a portion of the threaded member 107 positioned below at least one locking tooth 200, the locking tooth/teeth 200 provides an interference or barrier against at least subsequent axial displacement of the second bolster device 104b out of the associated aperture 152. Additionally, at least a portion of the threaded member 107 and/or locking tooth/teeth 200 may be positioned such that the threaded member 107 is in pressing engagement with the locking tooth/teeth 200, or another force is provided between the threaded member 107 and locking tooth/teeth 200, that prevents at least rotational displacement of the second bolster device 104b relative to the bone plate 154.

Additionally, similar to the engagement between the retention tab 105 and the one or more locking lobes or teeth 200 in the aperture 152 of the bone plate 154, the engagement between the threaded member 107 and the one or more locking lobes or teeth 200 in the aperture 152 can also at least assist in retaining the second bolster device 104b in position relative to at least the bone plate 154 including, for example, in instances in which the tension on the fractured bones that is provided by use of the bone plate 154 and associated bone screws changes. For example, engagement between the threaded member 107 and the one or more locking lobes or teeth 200 can at least assist in preventing the second bolster device 104b from being displaced away from, or at least partially popping out of, the bone plate 154.

Figure 15C:
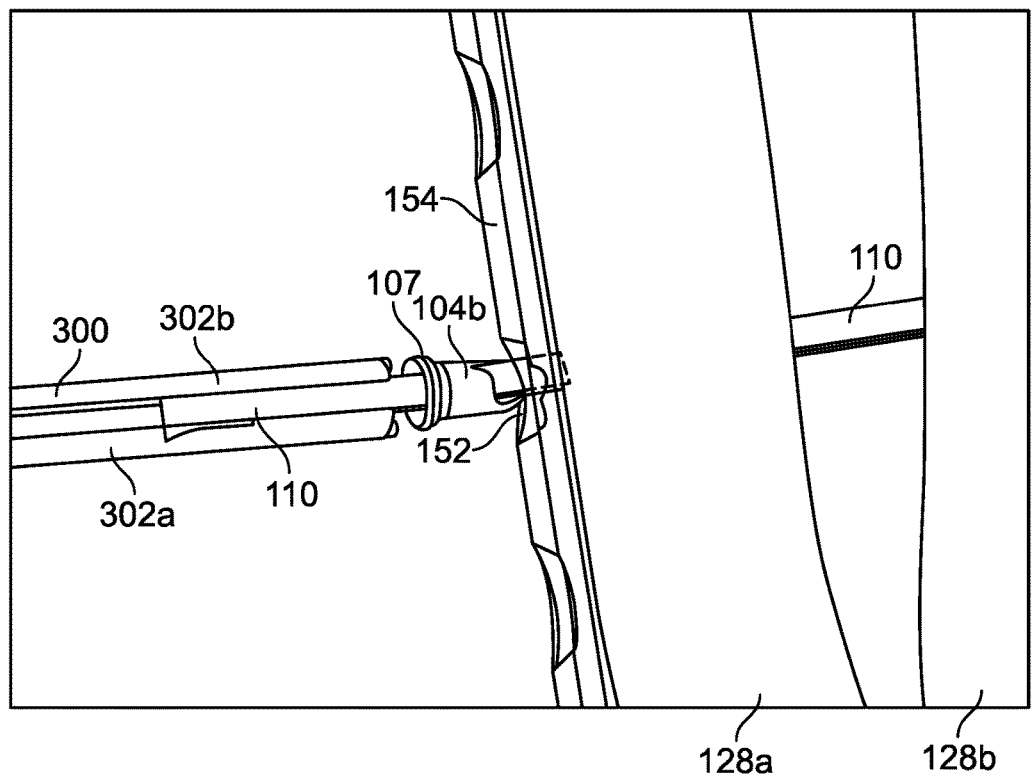
FIG. 15C illustrates a second bolster device engaged with an exemplary driver as the second bolster device is being displaced into engagement with an exemplary bone plate.
Figure 15D:
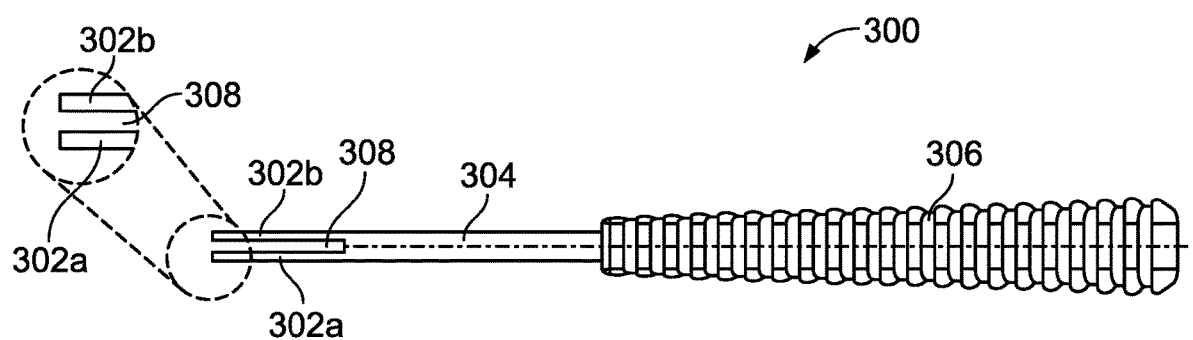
FIG. 15D illustrates a side view of an embodiment of a driver configured for driving engagement with a second bolster device.

As shown in FIGS. 7A-8, according to certain embodiments, the second bolster device 104a, 104b can also include one or more driver surfaces 109 that are shaped to facilitate engagement between the second bolster device 104a, 104b and a driver 300 (FIGS. 15C and 15D). For example, according to the illustrated embodiments, the driver surfaces 109 can be positioned to form one or more recesses 111 in second bolster device 104a, 104b that can each receive an arm 302a, 302b of the driver 300. According to the exemplary embodiment shown in FIGS. 15C and 15D, the arms 302a, 302b of the driver 300 can extend from a shaft 304 that is coupled to a handle 306. The arms 302a, 302b can be separated from each other by a gap 308. The gap 308 and/or recesses 111 may be sized to accommodate at least a portion of the arms 302a, 302b being received in a corresponding recess 111. Further, the gap 308 can extend along a length of the shaft 304 so as to accommodate at least a portion of the tether 110 of the bolster system 100 being received within the gap while the driver 300 is operably engaged with the second bolster device 104a, 104b. With the driver 300 is operably engaged with the second bolster device 104a, 104b, and with the arms 302a, 302b each positioned in a recess 111 of the second bolster device 104a, 104b, a user may rotate the driver 306 such as by gripping the handle 306. Depending on the direction of rotation, such rotation of the driver 300 will be translated to the second bolster device 104a, 104b via the arms 302a, 302b engaging one or more of the driver surfaces 109. Further, such rotation of the second bolster device 104a, 104b can, when the second bolster device 104a, 104b is being inserted into an aperture 152 of the bone plate 154 (FIG. 15C), facilitate the retention tab 105 or threaded member 107 being rotated to a position in which the retention tab 105 or threaded member 107 is positioned between one or more locking teeth 200 and an adjacent bone 128a, thereby at least assisting in locking the position of the second bolster device 104a, 104b relative to the bone plate 154, as discussed in detail above.

While the retention tab 105, the threaded member 107, the driver surfaces 109, and the recesses 111 are discussed and illustrated in connection with certain exemplary second bolster devices 104a, 104b, such features can also be incorporated into other bolster devices including, for example, the second bolster devices 104, 104', 104" illustrated in FIGS. 1A-6D, among other devices. Similarly, the features discussed herein with respect to the second bolster devices 104, 104', 104" illustrated in FIGS. 1A-6D can be incorporated into the second bolster devices 104a, 104b shown in FIGS. 7A-8, among other devices.

Additionally, the second bolster device 104, 104', 104", 104a, 104b can be secured within the bone plate 154 at a variety of different angles while still being recessed within at least the bone plate 154. Such variability can provide a degree of patient-to-patient variability. For example, according to certain embodiments, the second bolster device 104, 104', 104", 104a, 104b can have a size and/or shape that can accommodate the second bolster device 104, 104', 104", 104a, 104b having up to 15 degrees of freedom relative to at least the aperture 152 of the bone plate 154. Further, the number of locking teeth 200 for an aperture 152 can vary and can include, for example, five or six locking teeth 200, among other numbers of locking teeth 200.

Figure 9:
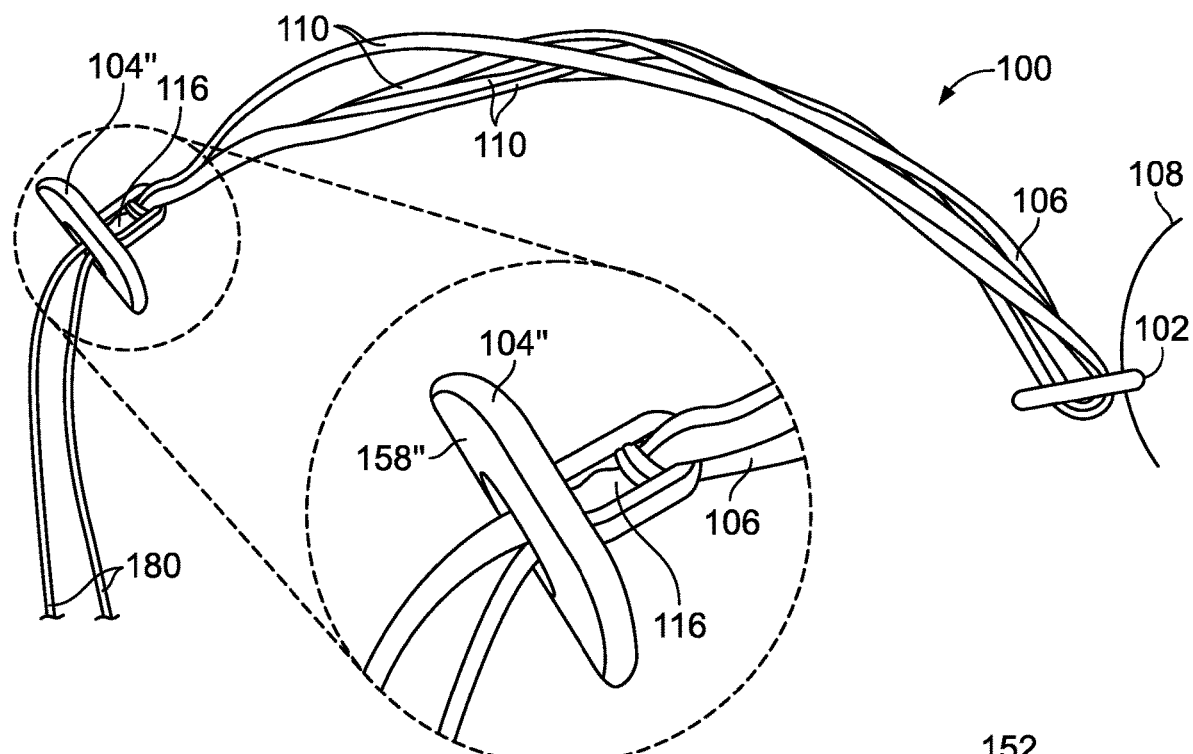
FIG. 9 illustrates a side view of a bolster system that includes the second bolster device from FIGS. 6A and 6B.

FIG. 9 illustrates an example of a second bolster device 104" secured to an adjustable tether 106 prior to implantation in a patient. As shown, the pre-tied slideable locking knot 116 is positioned or embedded within the channel 147" such that the pre-tied slideable locking knot 116 is positioned adjacent to the bridge portion 178 of the second bolster device 104 at the base portion 162 of the channel 147". Accordingly, as previously discussed, the channel 147" can have one or more sizes such as, for example, a diameter and depth that accommodate placement of the pre-tied slideable locking knot 116 in the channel 147". Additionally, the channel 147" can also have a depth that prevents ends 180 of the adjustable tether 106 that extend from beyond the pre-tied slideable locking knot 116 from extending beyond the inlet 145 of the second bolster device 104, 104', 104" when the bolster system 100 is implanted in a patient. Moreover, at least a portion of the ends 180 of the adjustable tether 106 can be removed or cut when the bolster system 100 is operably positioned or secured to a patient. Thus, the channel 147" can have a depth that permits the remaining portions of the cut ends 180 that extend from the pre-tied slideable locking knot 116 from extending outside of the channel 147", thereby at least attempting to prevent the ends 180 from engaging the patient in a manner that can result in irritation to the patient.

Figure 11:
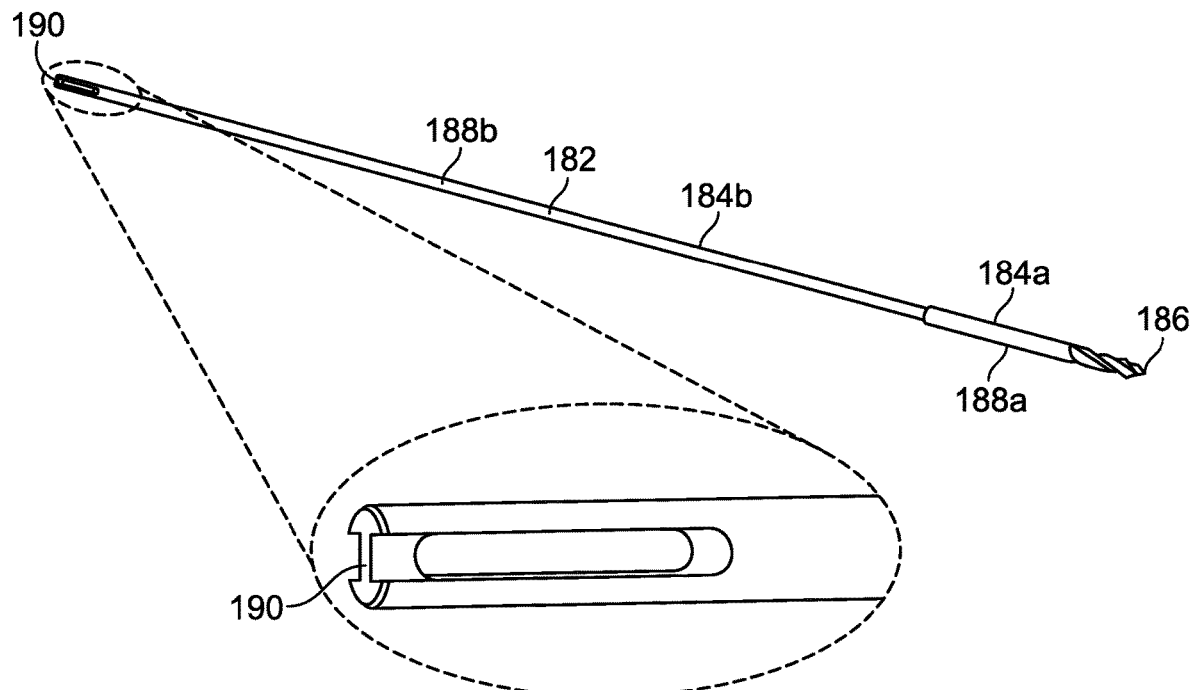
FIG. 11 illustrates an exemplary drill bit configured for use with a bolster system of the present invention.

FIG. 11 illustrates a drill bit 182 for use with the bolster system 100. According to certain embodiments, the drill bit 182 can include a first section 184a and a second section 184b, the first section 184a having a size such as, for example, a diameter that is larger than a corresponding size of the second section 184b. According to the illustrated embodiment, the first section 184a can extend from a first end 186 of the drill bit 182 and can include at least the cutting edge and flutes of the drill bit 182. For example, according to certain embodiments, the first section 184a of the drill bit 182 can provide the cutting surface and flute for a 3.5 millimeter drill bit. Further, according to certain embodiments, the first section 184a can include a first shank portion 188a and the second portion 184b can include a second shank portion 188b, with the first shank portion 188a having an outer size that is larger than a corresponding outer size of the second shank portion 188b. The portion of the second shank portion 188b that is in proximity to the second end 190 of the drill bit 182 can include an eyelet 192 that extends through at least a portion of, or extends from, the second shank portion 188b. For example, the eyelet 192 can extend from the second shank portion 188b and have an outer size such as, for example, a diameter which is smaller than a corresponding size of the second shank portion 188b. The eyelet 192 is configured to provide an opening through which the lead suture 108 can extend in a manner that can accommodate the lead suture being coupled to the drill bit 182. For example, the lead suture 108 can be tied to itself such that the lead suture 108 forms a generally continuous loop that extends through the eyelet 192, as well as through one or more tether apertures 130a, 130b in the first bolster device 102.

Figure 12:
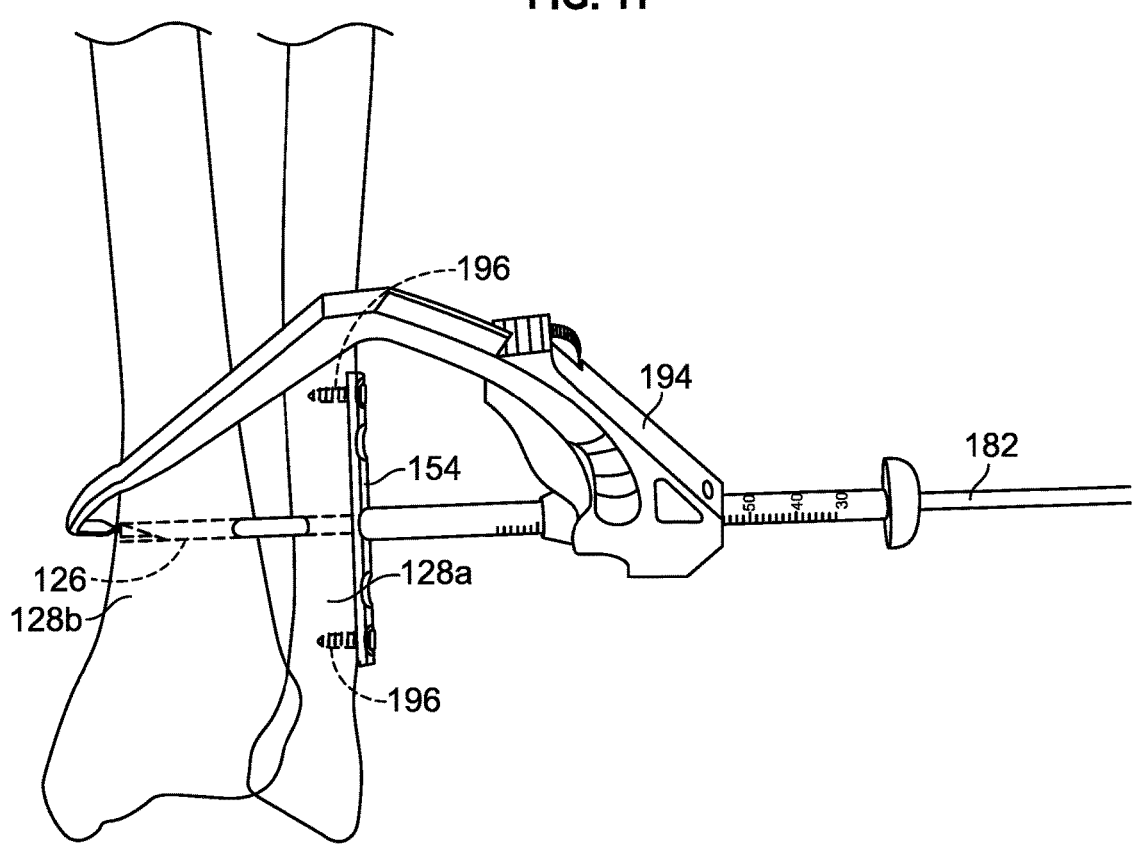
FIG. 12 illustrates use of an exemplary drill guide to guide the location and trajectory of drilling by a drill bit through one or more bones in connection with forming a passageway through the bone(s).

FIG. 12 illustrates use of an exemplary drill guide 194 to guide the location of drilling by the drill bit 182 through one or more bones 128a, 128b in connection with forming a passageway 126 through the bone(s) 128a, 128b. According to the illustrated embodiment, prior to drilling of the passageway 126, the bone plate 154 (shown in FIGS. 10A and 10B) can be secured to an exterior surface of a bone 128a through the insertion of one or more fixation devices 196, such as screws, through apertures 152 in the bone plate 154 and into drilled holes in the bone 128a. According to such embodiment, as previously discussed, the bolster system 100, including at least certain embodiments of the second bolster device 104, 104', 104a, 104b, among others, can be received within an aperture 152 in the bone plate 154. However, according to other embodiments, the bolster system 100 can be utilized in a patient without the inclusion of a bone plate 154.

Figure 10A:
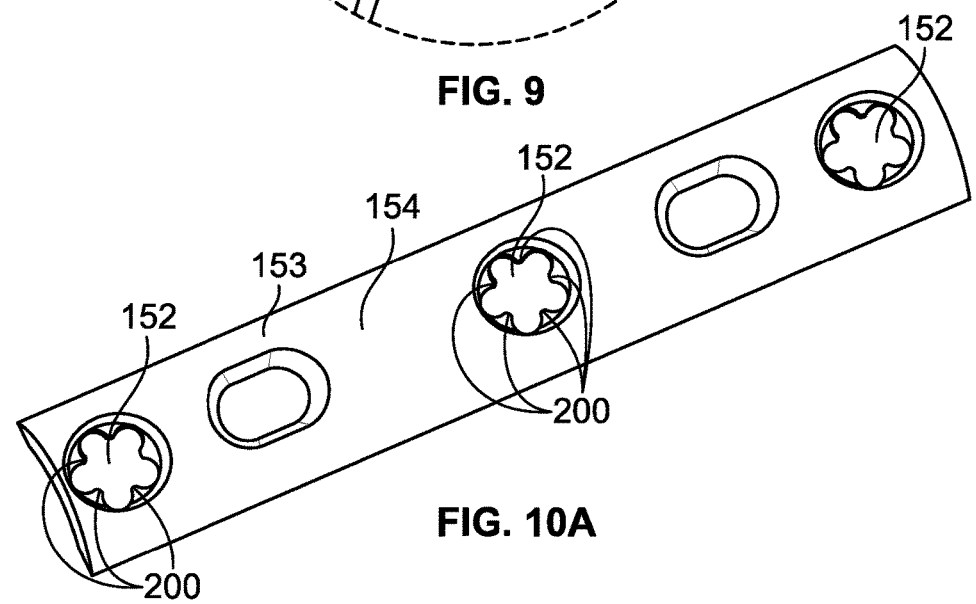
FIGS. 10A and 10B illustrate an outer side perspective view and a rear side view, respectively, of an exemplary bone plate for use with a bolster system of the present invention.
Figure 10B:
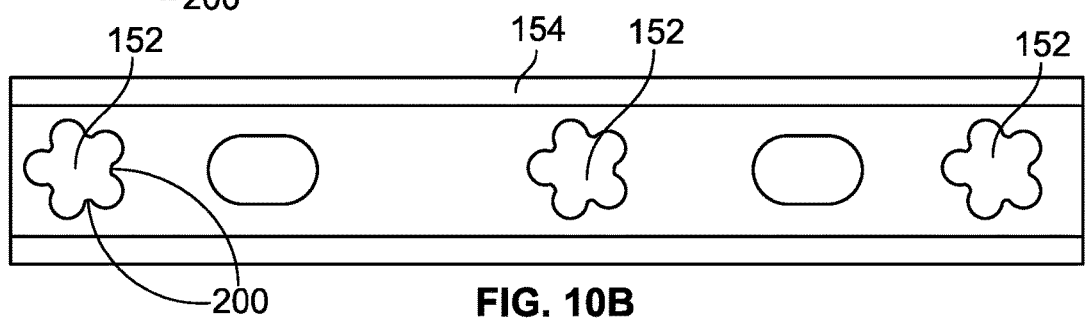
Figure 13A:
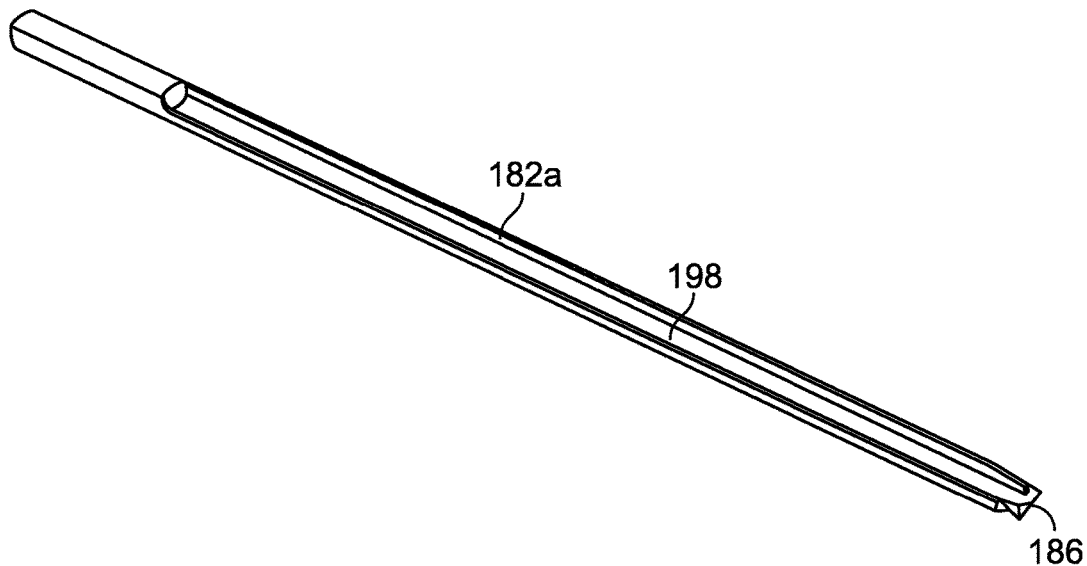
FIG. 13A illustrates a perspective view of an exemplary first drill bit that can provide a guide for a second drill bit in connection with shaping a cross-sectional shape and/or size of a passageway in one or more bones.
Figure 13B:
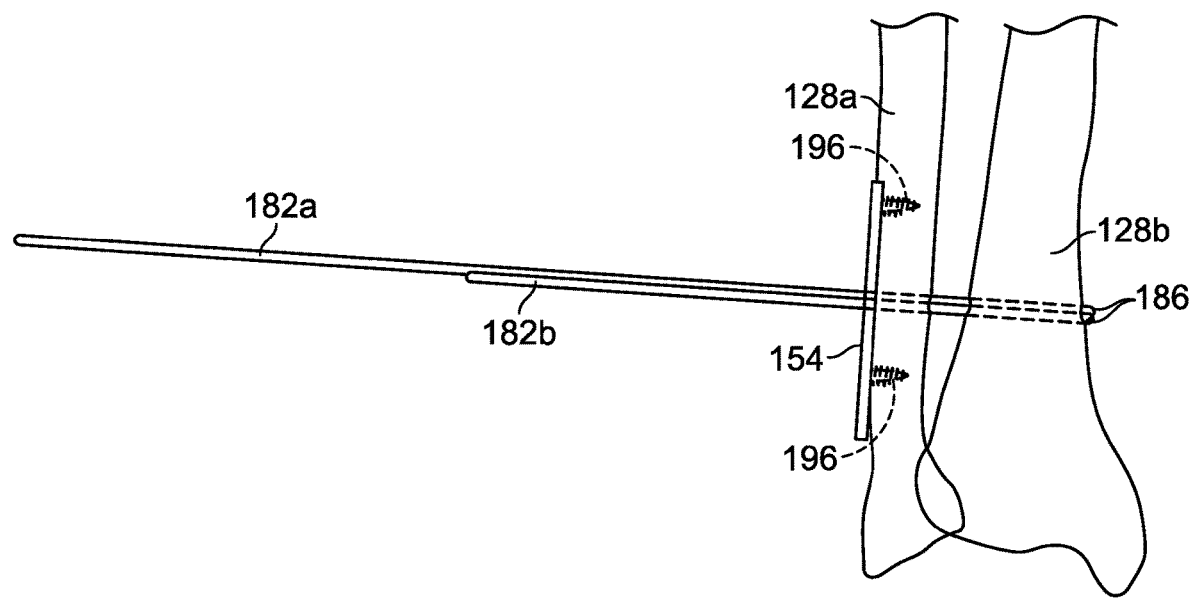
FIG. 13B illustrates a second drill bit positioned along a slot of the first drill bit of FIG. 13A as the second drill it is removing bone material in connection with shaping a passageway in one or more bones.

The drill guide 194 can be configured to be used with, or without, a separate drill clamp, and can be positioned along the bone(s) 128a, 128b at a location in which drill bit 182, when operably coupled to the drill guide 194, will drill or otherwise form the passageway 126 along a pre-determined trajectory and/or at pre-determined location within the bone(s) 128a, 128b. The drill bit 182 can also be, if not already, coupled to a drill (not shown) such that operation of the drill rotates the drill bit 182 in an manner in which the drill bit 182 can cut into the bone(s) 128a, 128b to form the passageway 126. Referencing FIG. 12, according to the illustrated embodiment, the drill bit 182 can be operated by operation of the drill to cut through the four cortices of the fibula 128a and tibia 128b The passageway 126 can be provided with a variety of different shapes and/or sizes. For example, according to certain embodiments, the passageway 126 can generally have a circular cross-sectional shape that is provided by the drill bit 182. According to other embodiments, the size and/or shape of the passageway 126 can be altered via the use of one or more other cutting or shaping instruments or components. For example, FIGS. 13A and 13B illustrate a cutting guide that can be used with at least the drill bit 182b to provide the passageway 126 in the bone 128a, 128b with a non-round cross-sectional shape such as, for example, an oval shape. For example, according to certain embodiments, the cutting guide can include a first drill bit 182a (FIG. 13A) that has a vertical slot 198 and which is used to drill a first hole in the bone 128a, 128b that has a generally circular cross-sectional shape. A second drill bit 182b (FIG. 13B) can then be positioned to extend along the slot 198 of the first drill bit 182a as the second drill bit 182b removes additional bone material from the bone(s) 128a, 128b at a location that at least extends from one side of the hole that was formed in the bone(s) 128a, 128b by the first drill bit 182a. The combination of holes formed by the first and second drill bits 182a, 182b can thereby form a passageway 126 having a generally elongated and/or oval shape. Such non-round shapes can be particularly suited for forming holes which are large enough to accommodate the insertion of at least a portion of the body portion 150, 150', 150" of the second bolster device 104, 104', 104", but which are also constrained by the size of the aperture 152 of a bone plate 154 such as, for example, at a location between locking teeth 200 in the aperture 152 of the bone plate 154 (FIGS. 10A and 10B). Alternatively, rather than utilizing first and second drill bits 182a, 182b, a single drill bit having a short cutting surface and flat surfaces that can fit between the locking teeth 200 in the aperture 152 of the bone plate 154 can be used.

Figure 14A:
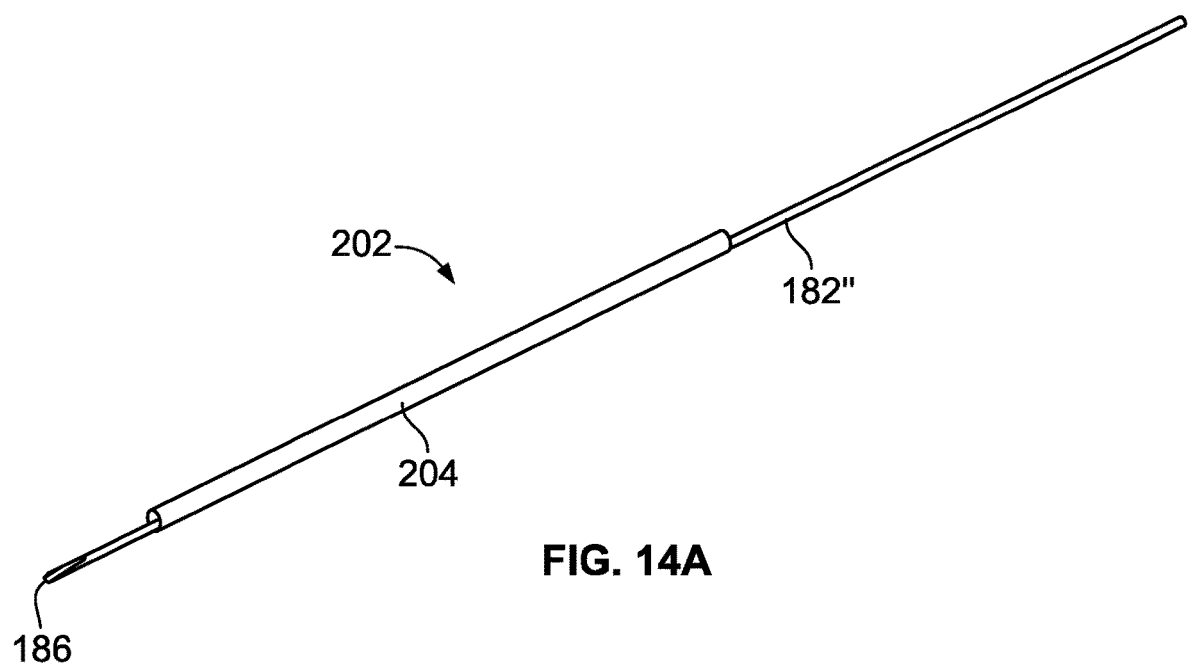
FIG. 14A illustrates a side perspective view of an exemplary shaping apparatus structured to form a cross-sectional shape and/or size of a passageway in one or more bones.
Figure 14B:
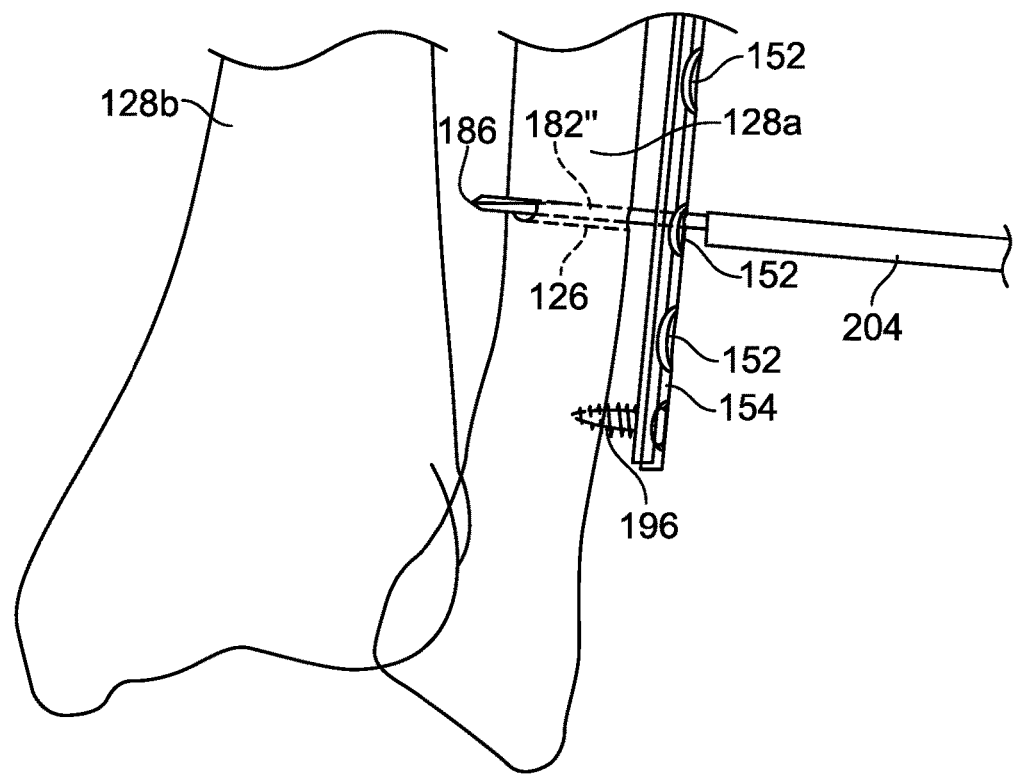
FIG. 14B illustrates an example of the shaping apparatus shown in FIG. 14A being inserted into a bone of a patient.

FIGS. 14A and 14B illustrate another shaping apparatus 202 structured to form a cross-sectional shape and/or size of a passageway through one or more bones 128a, 128b. According to such embodiments, the shaping apparatus 202 includes a drill bit 182" that drills through the cortices of one or more of the bones 128a, 128b. The shaping apparatus 202 can further include a chisel 204 that can slide over the drill bit 182" or otherwise be displaced with the drill bit 182", and through the hole formed by the drill bit 182". According to such an embodiment, after the drill bit 182" has established a hole through the bones 128a, 128b, the chisel 204 can pass along or with the drill bit 182" and through the aperture 152 in the bone plate 154. For example, according to certain embodiments, the chisel 204, which can have an ovular cross-sectional shape, can be displaced along the drill bit 182" in a direction that is generally tangential to locking teeth 200 in the aperture 152 of the bone plate 154. According to such an embodiment, the drill bit 182" can guide displacement of the chisel 204 through the hole formed by the drill bit 182" as the chisel 204 is tapped with an impact device such as, for example, a hammer or another impact device, and thereby forming a generally oval, or non-round, shaped passageway 126.

With the passageway formed, the drill bit 182, 182a, 182b, 182" can be de-coupled from the drill, thereby exposing the eyelet 192. The lead suture 108, which can already be coupled to the first bolster device 102, can then be coupled to the drill bit 182, 182a, 182b, 182" such that, as the drill bit 182, 182a, 182b, 182" is pulled through the passageway 126, at least a portion of the lead suture 108 can also pass through the passageway 126. Referring to FIG. 13, with the lead suture 108 exposed through one side of the passageway 126, the first bolster device 102 can be oriented, if not already, at a first orientation so that the first bolster device 102 is oriented to pass into a first side 206a of and through the passageway 126. The first bolster device 102 can then be displaced through the passageway 126 by a pulling force on the drill bit 182, 182a, 182b, 182" and/or the lead suture 108. When the first bolster device 102 passes out of a second side 206b of the passageway 126, the first bolster device 102 can be manipulated to, if not already in, a second orientation that can abut the back side 131b of the first bolster device 102 against a bone 128b in a manner that prevents the return passage of the first bolster device 102 through the passageway, as shown in FIG. 14.

As previously mentioned, according to certain embodiments, the pre-tied slideable locking knot 116 can be formed at least before the lead suture 108 and/or first bolster device 102 enters the passageway 126. Additionally, according to certain embodiments, the pre-tied slideable locking knot 116 can be pre-formed such as that the pre-tied slideable locking knot 116 is, and remains, embedded in the second bolster device 104, 104', 104" including, for example, embedded in the second bolster device 104, 104', 104" prior to the first bolster device 102 entering into the passageway 126. Thus, when the first bolster device 102 is positioned and oriented for operable abutment against a portion of the adjacent bone 128b, one or more ends 180 of the adjustable tether 106 can be pulled so as to at least axially displace the pre-tied slideable locking knot 116 from a first position to a second position so that the bolster system 100 exerts tension on the fibula and tibia in a manner that can at least assist in the repair of the tibiofibular joint. Further, according to certain embodiments in which the pre-tied slideable locking knot 116 is embedded in the second bolster device 104, 104', 104", such displacement of the pre-tied slideable locking knot 116 can be relative to the adjustable tether 106, as the pre-tied slideable locking knot 116 can generally be at a relatively static position relative to the second bolster device 104, 104', 104" and/or subjected to minimal axial displacement generally in a direction the along the central axis 148, 148', 148" within the second bolster device 104, 104', 104".

Alternatively, according to certain embodiments, when tightened, the pre-tied slideable locking knot 116 can be axially displaced from a first position at which the pre-tied slideable locking knot 116, or a portion of the pre-tied slideable locking knot 116, is positioned outside of the second bolster device 104, 104', 104", to a second position in which the pre-tied slideable locking knot 116 is recessed inside of the second bolster device 104, 104', 104". Additionally, according to certain embodiments, the second bolster device 104, 104', 104" can be positioned such that at least a portion of the second bolster device 104, 104', 104" extends into the passageway 126 and/or aperture 152 of the bone plate 154 prior to displacement of the pre-tied slideable locking knot 116 from the first position to the second position. Further, when at the second position, the pre-tied slideable locking knot 116 can be positioned or embedded in the channel 147, 147', 147" of the second bolster device 104, 104', 104" at a location in which the pre-tied slideable locking knot 116 abuts against or is otherwise in close proximity to the bridge portion 178 at the base of the channel 147, 147', 147" of the second bolster device 104, 104', 104". Further, the pre-tied slideable locking knot 116 is configured to prevent the pre-tied slideable locking knot 116 from returning from the second position to the first position along the adjustable tether 106 so as to at least assist the bolster system 100 in maintaining tension on fibula and tibia.

While the preceding examples and figures are discussed with respect to syndemosis repairs, it should be understood that the bolster system 100 can be utilized for repairs to a variety of other joints and/or bones. For example, as illustrated by FIGS. 16A-16C, the bolster system 100 can extend through adjacent metacarpal bones 208a, 208b of a wrist or hand 210. According to the illustrated example, a passageway can be drilled or otherwise formed through the first and second metacarpal bones 208a, 208b that is sized to accommodate the passage of a first bolster device 102 when the first bolster device 102 is in a first orientation. Again, the adjustable tether 106 can be operably secured to the first device 102 prior to insertion of the first device 102 into the drilled or otherwise formed passageway in the first and second metacarpal bones 208a, 208b. Further, the second bolster device 104''' can be operably secured to the adjustable tether 106 by the pre-tied slideable locking knot 116 prior to insertion of the first bolster device 102 into the first and second metacarpal bones 208a, 208b. Moreover, according to certain embodiments, the pre-tied slideable locking knot 116 can be formed such that the pre-tied slideable locking knot 116 is embedded within the second bolster device 102, wherein the pre-tied slideable locking knot 116 can remain at least before, during, and after the first bolster device 102 has been inserted into and through the passageway in the first and second metacarpal bones 208a, 208b, as well as before and during the displacement of the pre-tied slideable locking knot 116 from the first position to the second position relative to at least the adjustable tether 106. Accordingly, similar to the previously discussed examples, upon exiting the passageway of the first metacarpal bone 208a, the first bolster device 102 can be manipulated to a second position that prevents the first bolster device 102 from passing back through the passageway. With the first bolster device 102 in the second position, the first and/or second ends 112, 114 of the adjustable tether 106 can be pulled, thereby reducing a length of the adjustable tether 106 that extends between at least the pre-tied slideable locking knot 116 and the first bolster device 102, and thereby displacing the slideable locking knot 116 from the first position to the second position relative to at least the adjustable tether 106.

Figure 17A:
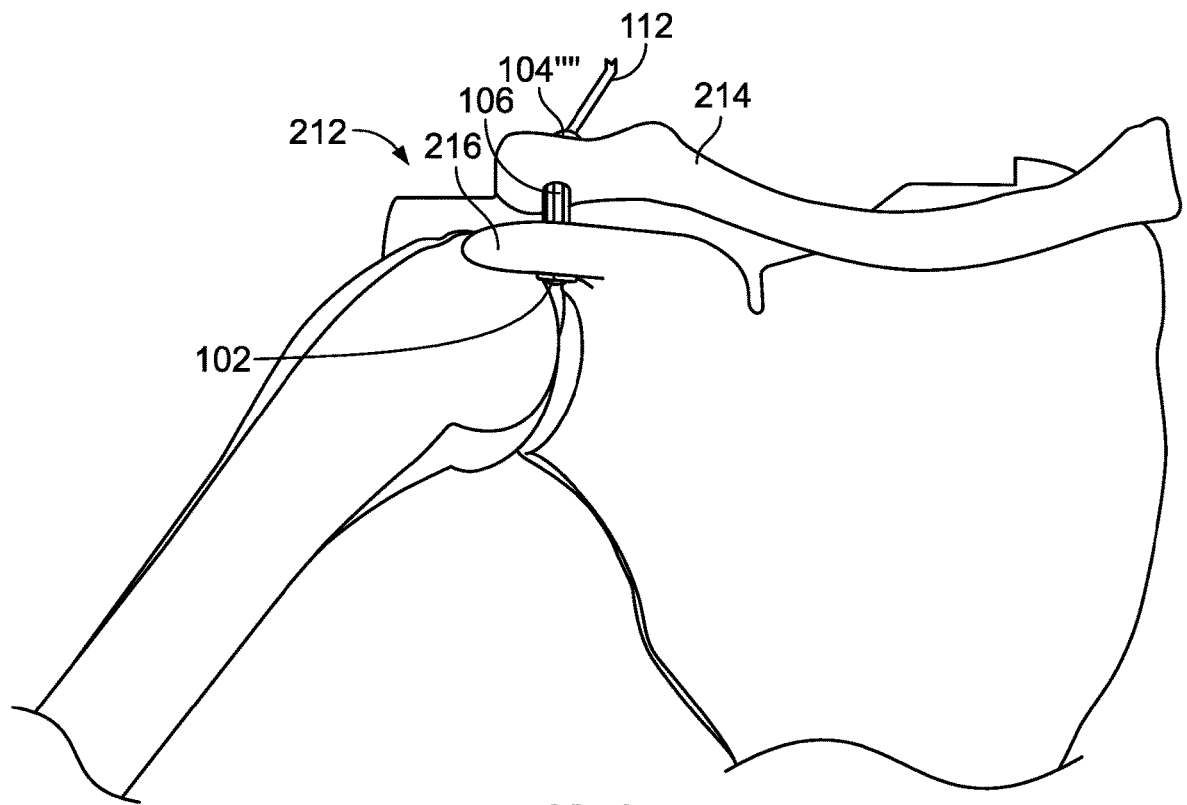
FIGS. 17A and 17B illustrate a side view and a phantom side view, respectively, of a bolster system used in connection with repairs to an acromioclavicular joint.
Figure 17B:
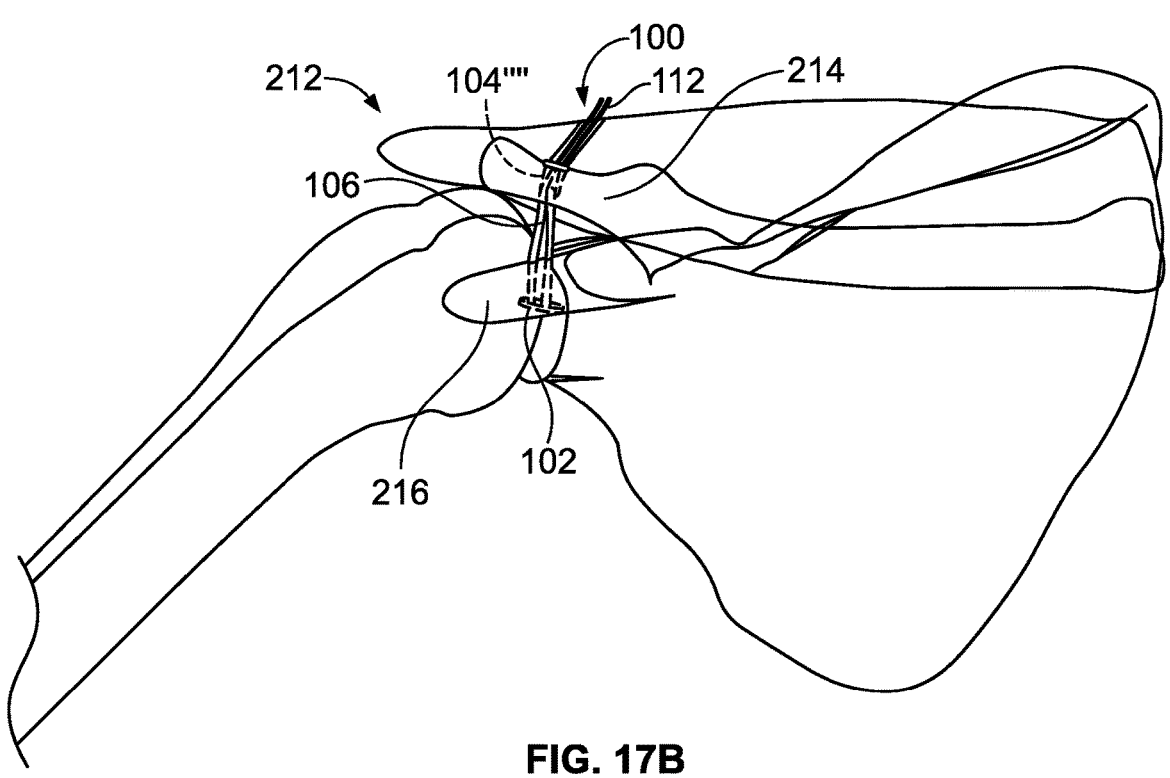

FIGS. 17A and 17B illustrate an additional, non-limiting use of the bolster system 100 in the repair of joints and/or bones. Moreover, as shown in FIGS. 17A and 17B, the bolster system 100 can also be used in association with the repair of a shoulder such as, for example, repair of acromioclavicular (AC) joints 212. As shown, in at least certain situations, implantation of the bolster system 100 can include passing the first bolster device 102 at a first orientation through a passageway drilled or otherwise formed in the clavicle 214 and the acromion 216. With the first bolster device 102 extending out of the passageway and beyond the acromion 216, the first bolster device 102 can be manipulated to a second orientation that prevents the first bolster device 102 from passing back through the passageway. While a variety of different shaped and sized first bolster devices 102 can be used with the bolster system 100, according to certain embodiments, relatively small bolster devices 102 may be used such as, for example, bolster devices 102 having a width of about 3.5 millimeters (mm). The first and/or second ends 112, 114 of the adjustable tether 106 can be pulled, thereby reducing a length of the adjustable tether 106 that extends between at least the pre-tied slideable locking knot 116 and the first bolster device 102, and thereby displacing the slideable locking knot 116 from the first position to the second position relative to at least the adjustable tether 106 such that pre-tied slideable locking knot 116 is tightened at the second position. Moreover, the first and/or second ends 112, 114 of the adjustable tether 106 can be pulled such that the pre-tied slideable locking knot 116 is tightened in a manner that prevents the length of the adjustable tether 106 between the first bolster device 102 and at least the pre-tied slideable locking knot 116 and/or the second bolster device 104"" from subsequently increasing.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law.

Furthermore it should be understood that while the use of the word preferable, preferably, or preferred in the description above indicates that feature so described can be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An apparatus, comprising:
a tether comprising a sliding knot;
a first bolster device coupled to the tether and configured to interface with a first bone; and
a second bolster device coupled to the tether, the second bolster device comprising:
a channel that receives the sliding knot;
a first aperture positioned at a first end of the channel; and
a second aperture positioned at the first end of the channel;
a bridge portion positioned at the first end of the channel between the first aperture and the second aperture, the bridge portion configured to abut the sliding knot; and
wherein a first portion of the tether extends into the channel via the first aperture, and wherein a second portion of the tether extends into the channel via the second aperture.

2. The apparatus of claim 1, wherein the second bolster device further comprises a body and a plate portion, the plate portion having a diameter greater than a diameter of the body portion.

3. The apparatus of claim 2, wherein the body portion is cylindrical.

4. The apparatus of claim 2, wherein the plate portion is circular in cross-section.

5. The apparatus of claim 2, wherein the plate portion is frustoconical.

6. The apparatus of claim 1, wherein the channel receives the sliding knot such that the sliding knot is recessed from an outer surface of the second bolster device.

7. The apparatus of claim 1, wherein the first bolster device is configured to directly interface with the first bone during an acromioclavicular repair procedure or a coracoclavicular repair procedure.

8. The apparatus of claim 1, wherein the second bolster device is configured to directly interface with a second bone during an acromioclavicular repair procedure or a coracoclavicular repair procedure.

9. An apparatus, comprising:
an adjustable tether;
a first bolster device coupled to the adjustable tether; and
a second bolster device coupled to the adjustable tether, the second bolster device comprising:
a first aperture through which a first portion of the adjustable tether extends;
a second aperture through which a second portion of the adjustable tether extends; and
a bridge portion positioned between the first aperture and the second aperture, the bridge portion operable to abut a third portion of the adjustable tether.

10. The apparatus of claim 9, wherein the third portion of the adjustable tether comprises a knot.

11. The apparatus of claim 10, wherein the knot is a sliding knot.

12. The apparatus of claim 9, wherein the second bolster device further comprises a channel connected with the first aperture and the second aperture.

13. The apparatus of claim 12, wherein each of the first aperture and the second aperture is formed at a first end of the channel.

14. The apparatus of claim 13, wherein the second bolster device further comprises a plate portion defining a third aperture at a second end of the channel.

15. A method, comprising:
   forming a passageway through one or more bones;
   coupling a first bolster device with one of the bones via an adjustable tether, wherein the adjustable tether is coupled to the first bolster device and a second bolster device; and
   coupling the second bolster device with another of the bones via the adjustable tether, wherein coupling the second bolster device with the another of the bones comprises:
   positioning a first portion of the second bolster device that has a first diameter in the passageway;
   positioning a second portion of the second bolster device that has a second diameter greater than the first diameter outside of the passageway and in abutment with the another of the bones; and
   abutting a knot coupled to the adjustable tether with a bridge portion of the second bolster device, the bridge portion positioned between a first aperture at a first end of the second bolster device and a second aperture at the first end of the second bolster device.

16. The method of claim 15, wherein the method is performed during an acromioclavicular repair procedure.

17. The method of claim 15, wherein the method is performed during a coracoclavicular repair procedure.

18. The method of claim 15, further comprising positioning the knot in the second bolster device such that the knot is recessed relative to an outer surface of the second bolster device.

* * * * *